United States Patent
Gagner et al.

(10) Patent No.: US 11,576,676 B2
(45) Date of Patent: Feb. 14, 2023

(54) ANASTOMOSIS FORMATION WITH MAGNETIC DEVICES HAVING TEMPORARY RETENTION MEMBER

(71) Applicant: GT METABOLIC SOLUTIONS, INC., Wilmington, DE (US)

(72) Inventors: Michel Gagner, Montréal (CA); Todd A. Krinke, Buffalo, MN (US); Thierry Thaure, San Jose, CA (US)

(73) Assignee: GT METABOLIC SOLUTIONS, INC., Wilmington, DE (US)

(*) Notice: Subject to any disclaimer, the term of this patent is extended or adjusted under 35 U.S.C. 154(b) by 0 days.

(21) Appl. No.: 17/477,790

(22) Filed: Sep. 17, 2021

(65) Prior Publication Data

US 2022/0087678 A1 Mar. 24, 2022

Related U.S. Application Data

(60) Provisional application No. 63/080,363, filed on Sep. 18, 2020.

(51) Int. Cl.
*A61B 17/11* (2006.01)
*A61B 17/00* (2006.01)

(52) U.S. Cl.
CPC . *A61B 17/1114* (2013.01); *A61B 2017/00004* (2013.01); *A61B 2017/00876* (2013.01); *A61B 2017/1135* (2013.01)

(58) Field of Classification Search
None
See application file for complete search history.

(56) References Cited

U.S. PATENT DOCUMENTS

| | | | |
|---|---|---|---|
| 5,690,656 A | * | 11/1997 | Cope ............. A61B 17/1114 606/153 |
| 6,632,229 B1 | | 10/2003 | Yamanouchi |
| 6,719,768 B1 | | 4/2004 | Cole et al. |

(Continued)

FOREIGN PATENT DOCUMENTS

| EP | 1493391 B1 | 12/2009 |
|---|---|---|
| EP | 2207488 B1 | 9/2012 |

(Continued)

OTHER PUBLICATIONS

International Search Report for PCT/US2021/050879, dated Dec. 20, 2021, 3 pages.

*Primary Examiner* — Shaun L David
(74) *Attorney, Agent, or Firm* — Casimir Jones, SC; Robert A. Goetz

(57) ABSTRACT

Systems and methods for forming an anastomosis between two adjacent walls of a digestive tract are provided. The system can include a first and second magnetic implants that are configured to magnetically couple to each other through the two adjacent walls of the digestive tract to compress a portion of the two adjacent walls therebetween and form a necrotic area that becomes surrounded by a scarred edge following a healing time period. The system can also include a retention member that can extend outwardly from a corresponding one of the first and second magnetic implants, the retention member being configured to retain the first and second magnetic implants in position and prevent passage thereof through the necrotic area during the healing time period.

29 Claims, 28 Drawing Sheets

Specification includes a Sequence Listing.

(56) References Cited

U.S. PATENT DOCUMENTS

| | | | |
|---|---|---|---|
| 7,282,057 B2 | 10/2007 | Surti et al. | |
| 7,909,837 B2 | 3/2011 | Crews et al. | |
| 8,043,290 B2 | 10/2011 | Hamson et al. | |
| 8,262,680 B2 | 9/2012 | Swain et al. | |
| 8,506,516 B2 | 8/2013 | Kassab et al. | |
| 8,556,919 B2 | 10/2013 | Aguirre et al. | |
| 8,623,036 B2 | 1/2014 | Harrison et al. | |
| 8,679,139 B2 | 3/2014 | Aguirre et al. | |
| 8,685,046 B2 | 4/2014 | Viola | |
| 8,728,105 B2 | 5/2014 | Aguirre et al. | |
| 8,794,243 B2 | 8/2014 | Deem et al. | |
| 8,828,031 B2 | 9/2014 | Fox et al. | |
| 8,845,663 B2 | 9/2014 | Chmura | |
| 8,915,915 B2 | 12/2014 | Harrison et al. | |
| 9,168,041 B2 | 10/2015 | Zaritsky et al. | |
| 9,226,753 B2 | 1/2016 | Surti et al. | |
| 9,943,335 B2 | 4/2018 | Gitlard et al. | |
| 10,039,550 B2 | 8/2018 | Altman | |
| 10,182,821 B2 | 1/2019 | Lukin et al. | |
| 10,285,703 B2 | 5/2019 | Viola | |
| 10,342,544 B2 | 7/2019 | Bakos et al. | |
| 10,376,400 B2 | 8/2019 | Mcguckin, Jr. | |
| 10,448,954 B2 | 10/2019 | Mcweeney et al. | |
| 10,555,735 B2 | 2/2020 | Bakos et al. | |
| 10,568,630 B2 | 2/2020 | Hernandez et al. | |
| 10,624,643 B2 | 4/2020 | Hunt et al. | |
| 10,624,644 B2 | 4/2020 | Bakos et al. | |
| 10,631,865 B2 | 4/2020 | Bakos et al. | |
| 10,682,143 B2 | 6/2020 | Hernandez et al. | |
| 10,779,831 B2 | 9/2020 | Lukin et al. | |
| 10,813,642 B2 | 10/2020 | Beisel et al. | |
| 10,952,732 B2 | 3/2021 | Binmoeller et al. | |
| 2006/0036267 A1* | 2/2006 | Saadat | A61B 17/11 606/153 |
| 2006/0271107 A1* | 11/2006 | Harrison | A61B 17/11 606/237 |
| 2007/0276378 A1* | 11/2007 | Harrison | A61B 17/1789 606/309 |
| 2008/0114384 A1* | 5/2008 | Chang | A61B 17/1114 606/153 |
| 2008/0208224 A1* | 8/2008 | Surti | A61B 17/1114 606/153 |
| 2009/0048618 A1* | 2/2009 | Harrison | A61B 17/70 606/153 |
| 2009/0125042 A1* | 5/2009 | Mouw | A61B 17/1114 606/153 |
| 2009/0227828 A1* | 9/2009 | Swain | A61B 17/1114 600/12 |
| 2010/0036399 A1* | 2/2010 | Viola | A61B 17/11 606/153 |
| 2010/0179510 A1* | 7/2010 | Fox | A61B 17/3478 604/509 |
| 2011/0009886 A1* | 1/2011 | Gagner | A61B 17/1114 606/153 |
| 2011/0144560 A1* | 6/2011 | Gagner | A61B 17/221 604/8 |
| 2011/0160752 A1* | 6/2011 | Aguirre | A61B 17/1114 606/153 |
| 2011/0295055 A1* | 12/2011 | Albrecht | A61F 2/04 600/37 |
| 2011/0295285 A1* | 12/2011 | McWeeney | A61B 17/11 606/153 |
| 2013/0253548 A1* | 9/2013 | Harrison | A61B 17/11 606/153 |
| 2013/0325042 A1* | 12/2013 | Fabian | A61B 17/12099 606/153 |
| 2014/0236064 A1* | 8/2014 | Binmoeller | A61B 17/1114 604/8 |
| 2014/0309669 A1* | 10/2014 | Fabian | A61B 17/1114 606/153 |
| 2015/0057687 A1* | 2/2015 | Gittard | A61B 17/11 606/153 |
| 2015/0164508 A1* | 6/2015 | Hernandez | A61B 17/11 606/153 |
| 2015/0182224 A1* | 7/2015 | Altman | A61B 17/1114 606/153 |
| 2016/0022266 A1* | 1/2016 | Lukin | A61B 17/11 606/154 |
| 2016/0262761 A1* | 9/2016 | Beisel | A61B 17/1114 |
| 2016/0287257 A1 | 10/2016 | Fabian et al. | |
| 2016/0324523 A1* | 11/2016 | Lukin | A61B 50/30 |
| 2017/0035425 A1* | 2/2017 | Fegelman | A61B 17/1114 |
| 2017/0265866 A1 | 9/2017 | Ryou et al. | |
| 2018/0028186 A1* | 2/2018 | Yamanouchi | A61B 17/1796 |
| 2018/0214149 A1* | 8/2018 | Hunt | A61B 17/1114 |
| 2018/0214150 A1* | 8/2018 | Bakos | A61B 17/1114 |
| 2018/0214152 A1* | 8/2018 | Bakos | A61B 17/1114 |
| 2018/0296218 A1 | 10/2018 | Binmoeller et al. | |
| 2018/0361127 A1* | 12/2018 | Gray | A61F 2/848 |
| 2019/0133678 A1 | 5/2019 | Pate et al. | |
| 2019/0183507 A1 | 6/2019 | Baillargeon | |
| 2019/0261998 A1 | 8/2019 | Altman et al. | |
| 2019/0274687 A1* | 9/2019 | Wang | A61B 17/1114 |
| 2020/0008834 A1 | 1/2020 | Cauche et al. | |
| 2020/0129283 A1 | 4/2020 | Swensgard et al. | |
| 2020/0138438 A1* | 5/2020 | Harrison | A61B 17/1114 |
| 2020/0323530 A1 | 10/2020 | Sharma | |

FOREIGN PATENT DOCUMENTS

| | | |
|---|---|---|
| EP | 2538852 A1 | 1/2013 |
| EP | 3267905 A1 | 1/2018 |
| EP | 2260752 B1 | 3/2018 |
| EP | 3573542 A1 | 12/2019 |
| EP | 3487418 A4 | 4/2020 |
| WO | WO2014055193 A1 | 4/2014 |
| WO | WO2016082481 A1 | 6/2016 |
| WO | WO2019077218 A1 | 4/2019 |
| WO | WO2019232526 A1 | 6/2019 |
| WO | WO2019232527 A1 | 12/2019 |
| WO | WO 2021/207821 | 10/2021 |

* cited by examiner

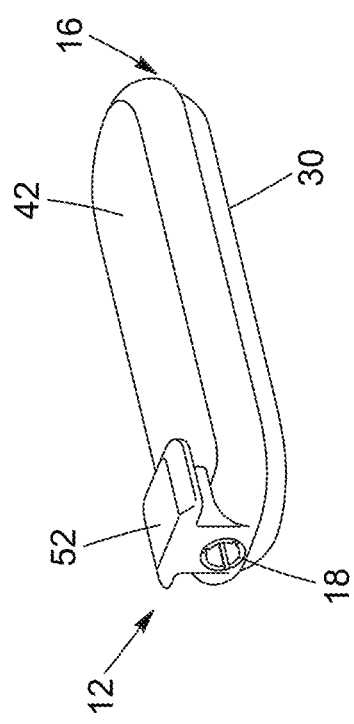
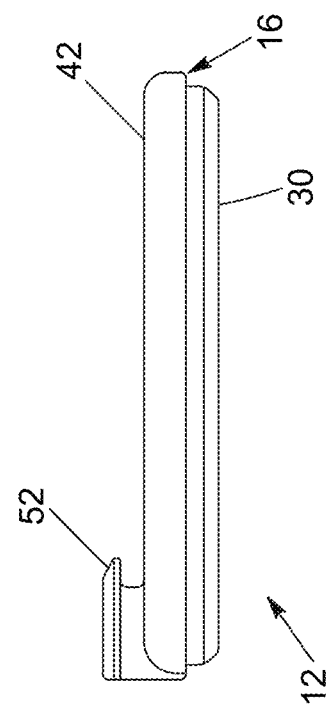

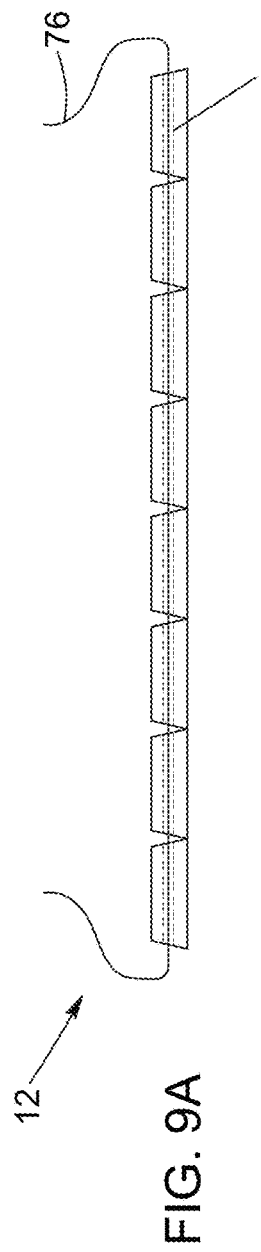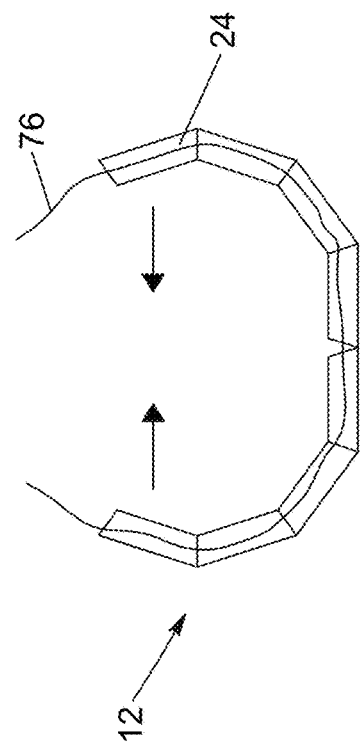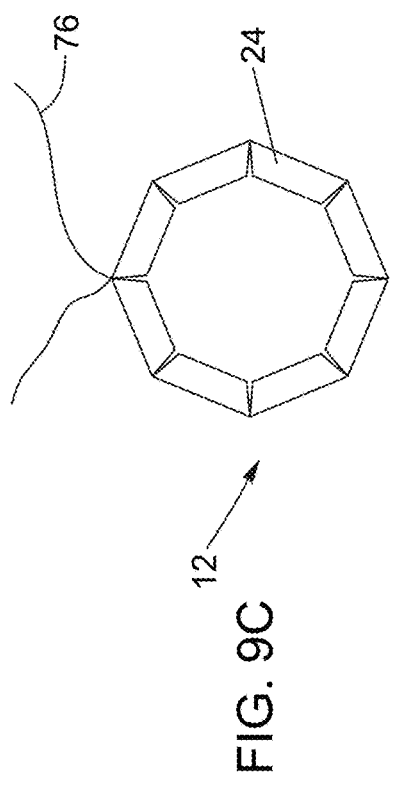

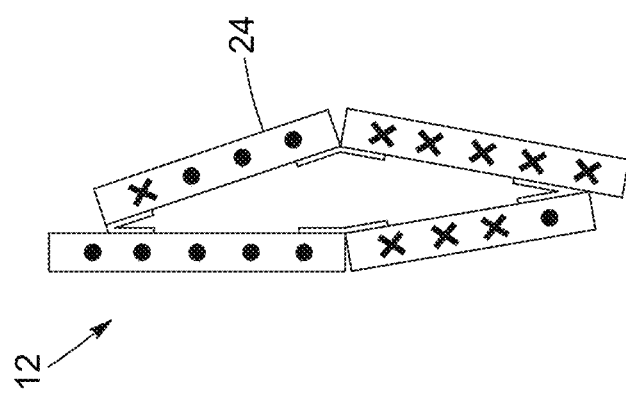
FIG. 11A
FIG. 11B
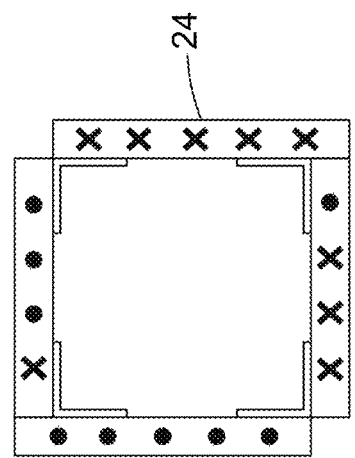
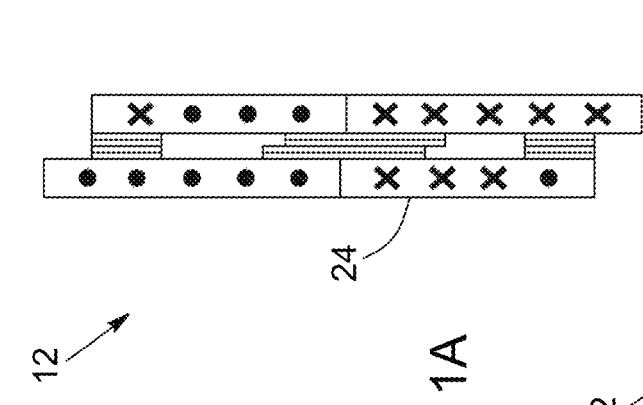
FIG. 11C
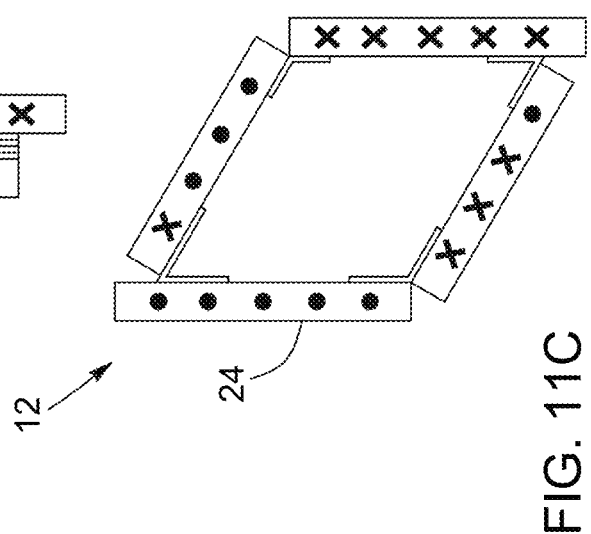
FIG. 11D

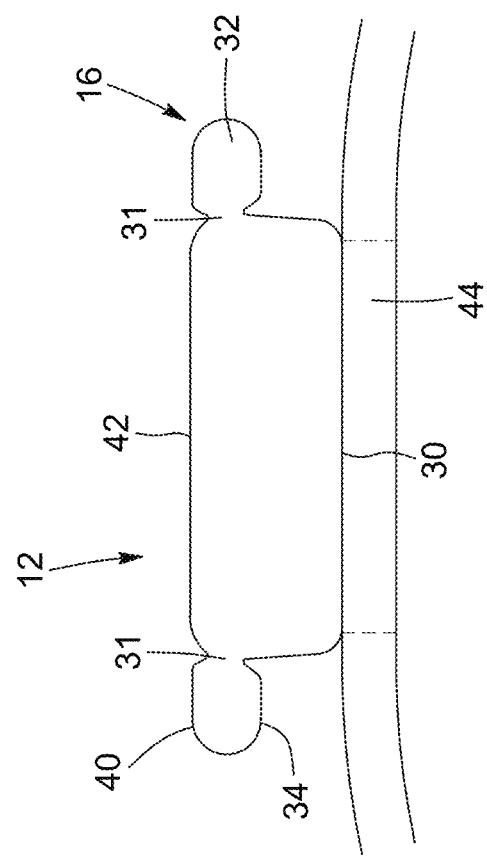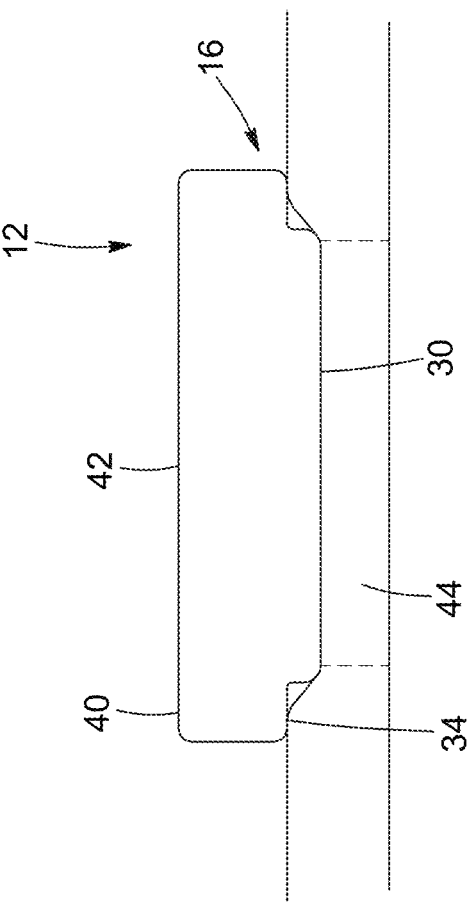

SEQUENCE LISTING

<160> NUMBER OF SEQ ID NOS: 51

<210> SEQ ID NO 1
<211> LENGTH: 30
<212> TYPE: PRT

```
<213> ORGANISM: Artificial Sequence
<220> FEATURE:
<223> OTHER INFORMATION: AG30

<400> SEQUENCE: 1

Met Leu Ser Leu Ile Phe Leu His Arg Leu Lys Ser Met Arg Lys Arg
1               5                   10                  15

Leu Asp Arg Lys Leu Arg Leu Trp His Arg Lys Asn Tyr Pro
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: AG30/5C

<400> SEQUENCE: 2

Met Leu Lys Leu Ile Phe Leu His Arg Leu Lys Arg Met Arg Lys Arg
1               5                   10                  15

Leu Lys Arg Lys Leu Arg Leu Trp His Arg Lys Arg Tyr Lys
            20                  25                  30

<210> SEQ ID NO 3
<211> LENGTH: 24
<212> TYPE: PRT
<213> ORGANISM: Artificial Sequence
<220> FEATURE:
<223> OTHER INFORMATION: AH90

<400> SEQUENCE: 3

Ala Thr Ala Trp Asp Phe Gly Pro His Gly Leu Leu Pro Ile Arg Pro
1               5                   10                  15

Ile Arg Ile Arg Pro Leu Cys Gly
            20

<210> SEQ ID NO 4
<211> LENGTH: 11
<212> TYPE: PRT
<213> ORGANISM: Artificial Sequence
<220> FEATURE:
<223> OTHER INFORMATION: CW49

<400> SEQUENCE: 4

Ala Pro Phe Arg Met Gly Ile Cys Thr Thr Asn
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Cys-KR12

<400> SEQUENCE: 5

Cys Lys Arg Ile Val Lys Arg Ile Lys Lys Trp Leu Arg
1               5                   10

<210> SEQ ID NO 6
<211> LENGTH: 21
<212> TYPE: PRT
<213> ORGANISM: Artificial Sequence
<220> FEATURE:
<223> OTHER INFORMATION: Esculentin-1a(1-21)

<400> SEQUENCE: 6
```

```
Gly Ile Phe Ser Lys Leu Ala Gly Lys Ile Lys Asn Leu Leu Ile
1               5                   10                  15

Ser Gly Leu Lys Gly
            20

<210> SEQ ID NO 7
<211> LENGTH: 36
<212> TYPE: PRT
<213> ORGANISM: Artificial Sequence
<220> FEATURE:
<223> OTHER INFORMATION: hBD-1

<400> SEQUENCE: 7

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
        35

<210> SEQ ID NO 8
<211> LENGTH: 41
<212> TYPE: PRT
<213> ORGANISM: Artificial Sequence
<220> FEATURE:
<223> OTHER INFORMATION: hBD-2

<400> SEQUENCE: 8

Gly Ile Gly Asp Pro Val Thr Cys Leu Lys Ser Gly Ala Ile Cys His
1               5                   10                  15

Pro Val Phe Cys Pro Arg Arg Tyr Lys Gln Ile Gly Thr Cys Gly Leu
            20                  25                  30

Pro Gly Thr Lys Cys Cys Lys Lys Pro
        35                  40

<210> SEQ ID NO 9
<211> LENGTH: 45
<212> TYPE: PRT
<213> ORGANISM: Artificial Sequence
<220> FEATURE:
<223> OTHER INFORMATION: hBD-3

<400> SEQUENCE: 9

Gly Ile Ile Asn Thr Leu Gln Lys Tyr Tyr Cys Arg Val Arg Gly Gly
1               5                   10                  15

Arg Cys Ala Val Leu Ser Cys Leu Pro Lys Glu Glu Gln Ile Gly Lys
            20                  25                  30

Cys Ser Thr Arg Gly Arg Lys Cys Cys Arg Arg Lys Lys
        35                  40                  45

<210> SEQ ID NO 10
<211> LENGTH: 37
<212> TYPE: PRT
<213> ORGANISM: Artificial Sequence
<220> FEATURE:
<223> OTHER INFORMATION: hBD-4

<400> SEQUENCE: 10

Glu Leu Asp Arg Ile Cys Gly Tyr Gly Thr Ala Arg Cys Arg Lys Lys
1               5                   10                  15

Cys Arg Ser Gln Glu Tyr Arg Ile Gly Arg Cys Pro Asn Thr Tyr Ala
            20                  25                  30
```

Cys Cys Leu Arg Lys
        35

<210> SEQ ID NO 11
<211> LENGTH: 38
<212> TYPE: PRT
<213> ORGANISM: Artificial Sequence
<220> FEATURE:
<223> OTHER INFORMATION: Histatin-1
<220> FEATURE:
<221> NAME/KEY: MISC_FEATURE
<222> LOCATION: (2)..(2)
<223> OTHER INFORMATION: Phosphoserine

<400> SEQUENCE: 11

Asp Ser His Glu Lys Arg His His Gly Tyr Arg Arg Lys Phe His Glu
1               5                   10                  15

Lys His His Ser His Arg Glu Phe Pro Phe Tyr Gly Asp Tyr Gly Ser
            20                  25                  30

Asn Tyr Leu Tyr Asp Asn
        35

<210> SEQ ID NO 12
<211> LENGTH: 27
<212> TYPE: PRT
<213> ORGANISM: Artificial Sequence
<220> FEATURE:
<223> OTHER INFORMATION: Histatin-2

<400> SEQUENCE: 12

Arg Lys Phe His Glu Lys His His Ser His Arg Glu Phe Pro Phe Tyr
1               5                   10                  15

Gly Asp Tyr Gly Ser Asn Tyr Leu Tyr Asp Asn
            20                  25

<210> SEQ ID NO 13
<211> LENGTH: 32
<212> TYPE: PRT
<213> ORGANISM: Artificial Sequence
<220> FEATURE:
<223> OTHER INFORMATION: Histatin-3

<400> SEQUENCE: 13

Asp Ser His Ala Lys Arg His His Gly Tyr Lys Arg Lys Phe His Glu
1               5                   10                  15

Lys His His Ser His Arg Gly Tyr Arg Ser Asn Tyr Leu Tyr Asp Asn
            20                  25                  30

<210> SEQ ID NO 14
<211> LENGTH: 12
<212> TYPE: PRT
<213> ORGANISM: Artificial Sequence
<220> FEATURE:
<223> OTHER INFORMATION: IDR-1018

<400> SEQUENCE: 14

Val Arg Leu Ile Val Ala Val Arg Ile Trp Arg Arg
1               5                   10

<210> SEQ ID NO 15
<211> LENGTH: 37
<212> TYPE: PRT
<213> ORGANISM: Artificial Sequence
<220> FEATURE:
<223> OTHER INFORMATION: LL-37

<400> SEQUENCE: 15

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 16
<211> LENGTH: 22
<212> TYPE: PRT
<213> ORGANISM: Artificial Sequence
<220> FEATURE:
<223> OTHER INFORMATION: MSI-78 (pexiganan)

<400> SEQUENCE: 16

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 17
<211> LENGTH: 20
<212> TYPE: PRT
<213> ORGANISM: Artificial Sequence
<220> FEATURE:
<223> OTHER INFORMATION: Pep19-2.5

<400> SEQUENCE: 17

Gly Cys Lys Lys Tyr Arg Arg Phe Arg Trp Lys Phe Lys Gly Lys Phe
1               5                   10                  15

Trp Phe Trp Gly
            20

<210> SEQ ID NO 18
<211> LENGTH: 38
<212> TYPE: PRT
<213> ORGANISM: Artificial Sequence
<220> FEATURE:
<223> OTHER INFORMATION: PLL-37

<400> SEQUENCE: 18

Pro Leu Leu Gly Asp Phe Phe Arg Lys Ser Lys Glu Lys Ile Gly Lys
1               5                   10                  15

Glu Phe Lys Arg Ile Val Gln Arg Ile Lys Asp Phe Leu Arg Asn Leu
            20                  25                  30

Val Pro Arg Thr Glu Ser
        35

<210> SEQ ID NO 19
<211> LENGTH: 19
<212> TYPE: PRT
<213> ORGANISM: Artificial Sequence
<220> FEATURE:
<223> OTHER INFORMATION: SHAP1

<400> SEQUENCE: 19

Ala Pro Lys Ala Met Lys Leu Leu Lys Lys Leu Leu Lys Leu Gln Lys
1               5                   10                  15

Lys Gly Ile

```
<210> SEQ ID NO 20
<211> LENGTH: 20
<212> TYPE: PRT
<213> ORGANISM: Artificial Sequence
<220> FEATURE:
<223> OTHER INFORMATION: SR-0007

<400> SEQUENCE: 20

Met Leu Lys Leu Ile Phe Leu His Arg Leu Lys Arg Met Arg Lys Arg
1               5                   10                  15

Leu Lys Arg Lys
            20

<210> SEQ ID NO 21
<211> LENGTH: 20
<212> TYPE: PRT
<213> ORGANISM: Artificial Sequence
<220> FEATURE:
<223> OTHER INFORMATION: SR-0379
<220> FEATURE:
<221> NAME/KEY: MISC_FEATURE
<222> LOCATION: (20)..(20)
<223> OTHER INFORMATION: D-Amino Acid

<400> SEQUENCE: 21

Met Leu Lys Leu Ile Phe Leu His Arg Leu Lys Arg Met Arg Lys Arg
1               5                   10                  15

Leu Lys Arg Lys
            20

<210> SEQ ID NO 22
<211> LENGTH: 13
<212> TYPE: PRT
<213> ORGANISM: Artificial Sequence
<220> FEATURE:
<223> OTHER INFORMATION: Temporin A

<400> SEQUENCE: 22

Phe Leu Pro Leu Ile Gly Arg Val Leu Ser Gly Ile Leu
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Temporin B

<400> SEQUENCE: 23

Leu Leu Pro Ile Val Gly Asn Leu Leu Lys Ser Leu Leu
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Col4-1

<400> SEQUENCE: 24

Met Phe Arg Lys Pro Ile Pro Ser Thr Val Lys Ala
1               5                   10

<210> SEQ ID NO 25
<211> LENGTH: 25
<212> TYPE: PRT
<213> ORGANISM: Artificial Sequence
```

```
<220> FEATURE:
<223> OTHER INFORMATION: Comb1

<400> SEQUENCE: 25

Asp Ile Asn Glu Cys Glu Ile Gly Ala Pro Ala Gly Glu Glu Thr Glu
1               5                   10                  15

Val Thr Val Glu Gly Leu Glu Pro Gly
            20                  25

<210> SEQ ID NO 26
<211> LENGTH: 36
<212> TYPE: PRT
<213> ORGANISM: Artificial Sequence
<220> FEATURE:
<223> OTHER INFORMATION: E1

<400> SEQUENCE: 26

Gly Glu Thr Gly Pro Ala Gly Pro Ala Gly Pro Ile Gly Pro Val Gly
1               5                   10                  15

Ala Arg Gly Pro Ala Gly Pro Gln Gly Pro Arg Gly Asp Lys Gly Glu
            20                  25                  30

Thr Gly Glu Gln
        35

<210> SEQ ID NO 27
<211> LENGTH: 11
<212> TYPE: PRT
<213> ORGANISM: Artificial Sequence
<220> FEATURE:
<223> OTHER INFORMATION: Tiger17

<400> SEQUENCE: 27

Trp Cys Lys Pro Lys Pro Lys Pro Arg Cys His
1               5                   10

<210> SEQ ID NO 28
<211> LENGTH: 23
<212> TYPE: PRT
<213> ORGANISM: Artificial Sequence
<220> FEATURE:
<223> OTHER INFORMATION: TP-508

<400> SEQUENCE: 28

Ala Gly Tyr Lys Pro Asp Glu Gly Lys Arg Gly Asp Ala Cys Glu Gly
1               5                   10                  15

Asp Ser Gly Gly Pro Phe Val
            20

<210> SEQ ID NO 29
<211> LENGTH: 14
<212> TYPE: PRT
<213> ORGANISM: Artificial Sequence
<220> FEATURE:
<223> OTHER INFORMATION: TSN1

<400> SEQUENCE: 29

Asn Phe Gln Gly Val Gln Asn Arg Phe Val Phe Gly Thr Pro
1               5                   10

<210> SEQ ID NO 30
<211> LENGTH: 16
<212> TYPE: PRT
<213> ORGANISM: Artificial Sequence
<220> FEATURE:
<223> OTHER INFORMATION: TSN2
```

<400> SEQUENCE: 30

Met Glu Asn Ala Glu Leu Asp Val Pro Ile Gln Ser Val Phe Thr Arg
1               5                   10                  15

<210> SEQ ID NO 31
<211> LENGTH: 11
<212> TYPE: PRT
<213> ORGANISM: Artificial Sequence
<220> FEATURE:
<223> OTHER INFORMATION: TSN3

<400> SEQUENCE: 31

Asn Thr Asp Asn Ile Tyr Pro Glu Ser Ser Cys
1               5                   10

<210> SEQ ID NO 32
<211> LENGTH: 8
<212> TYPE: PRT
<213> ORGANISM: Artificial Sequence
<220> FEATURE:
<223> OTHER INFORMATION: TSN4

<400> SEQUENCE: 32

Pro Tyr Leu Gly Tyr Val Phe Lys
1               5

<210> SEQ ID NO 33
<211> LENGTH: 18
<212> TYPE: PRT
<213> ORGANISM: Artificial Sequence
<220> FEATURE:
<223> OTHER INFORMATION: TSN5

<400> SEQUENCE: 33

Met Gln Thr Val Ala Gln Leu Phe Lys Thr Val Ser Ser Leu Ser Leu
1               5                   10                  15

Ser Thr

<210> SEQ ID NO 34
<211> LENGTH: 19
<212> TYPE: PRT
<213> ORGANISM: Artificial Sequence
<220> FEATURE:
<223> OTHER INFORMATION: TSN6

<400> SEQUENCE: 34

His Ser Pro Asp Ile Gln Leu Gln Lys Gly Leu Thr Phe Glu Pro Ile
1               5                   10                  15

Gln Ile Lys

<210> SEQ ID NO 35
<211> LENGTH: 16
<212> TYPE: PRT
<213> ORGANISM: Artificial Sequence
<220> FEATURE:
<223> OTHER INFORMATION: TSN7

<400> SEQUENCE: 35

Ser Thr Ile Thr Gln Pro Tyr Lys Thr Leu Asn Asn Ala Arg Ser Pro
1               5                   10                  15

<210> SEQ ID NO 36
<211> LENGTH: 15
<212> TYPE: PRT

```
<213> ORGANISM: Artificial Sequence
<220> FEATURE:
<223> OTHER INFORMATION: TSN8

<400> SEQUENCE: 36

Arg Pro Gly Pro Ser Pro Glu Gly Thr Gly Gln Ser Tyr Asn Tyr
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: TSN9

<400> SEQUENCE: 37

Met Glu Asn Ala Glu Leu Asp Pro Pro Tyr Leu Gly Tyr Val Phe Lys
1               5                   10                  15

<210> SEQ ID NO 38
<211> LENGTH: 20
<212> TYPE: PRT
<213> ORGANISM: Artificial Sequence
<220> FEATURE:
<223> OTHER INFORMATION: TSN10

<400> SEQUENCE: 38

Thr Gly Gln Ser Tyr Asn Gln Tyr Ser Gln Arg Pro Tyr Leu Gly Val
1               5                   10                  15

Tyr Val Phe Lys
            20

<210> SEQ ID NO 39
<211> LENGTH: 10
<212> TYPE: PRT
<213> ORGANISM: Artificial Sequence
<220> FEATURE:
<223> OTHER INFORMATION: TSN11

<400> SEQUENCE: 39

Leu Tyr Gly Gln Thr Pro Leu Glu Thr Leu
1               5                   10

<210> SEQ ID NO 40
<211> LENGTH: 11
<212> TYPE: PRT
<213> ORGANISM: Artificial Sequence
<220> FEATURE:
<223> OTHER INFORMATION: TSN12

<400> SEQUENCE: 40

Glu Leu Ala Asp Ser Pro Ala Leu Glu Ile Gly
1               5                   10

<210> SEQ ID NO 41
<211> LENGTH: 21
<212> TYPE: PRT
<213> ORGANISM: Artificial Sequence
<220> FEATURE:
<223> OTHER INFORMATION: TSN13

<400> SEQUENCE: 41

Leu Tyr Gly Gln Thr Pro Leu Glu Thr Leu Glu Leu Ala Asp Ser Pro
1               5                   10                  15

Ala Leu Glu Ile Gly
            20
```

<210> SEQ ID NO 42
<211> LENGTH: 14
<212> TYPE: PRT
<213> ORGANISM: Artificial Sequence
<220> FEATURE:
<223> OTHER INFORMATION: TSN14

<400> SEQUENCE: 42

Val Ser Gly Asn Thr Val Glu Tyr Ala Leu Pro Thr Leu Glu
1               5                   10

<210> SEQ ID NO 43
<211> LENGTH: 18
<212> TYPE: PRT
<213> ORGANISM: Artificial Sequence
<220> FEATURE:
<223> OTHER INFORMATION: TSN15

<400> SEQUENCE: 43

Leu Asp Ser Pro Thr Ala Pro Thr Val Gln Ser Thr Ala Leu Thr Trp
1               5                   10                  15

Arg Pro

<210> SEQ ID NO 44
<211> LENGTH: 17
<212> TYPE: PRT
<213> ORGANISM: Artificial Sequence
<220> FEATURE:
<223> OTHER INFORMATION: TSN16

<400> SEQUENCE: 44

Leu Asp Gly Ser Ala Pro Gly Pro Leu Tyr Thr Gly Ser Ala Leu Asp
1               5                   10                  15

Phe

<210> SEQ ID NO 45
<211> LENGTH: 11
<212> TYPE: PRT
<213> ORGANISM: Artificial Sequence
<220> FEATURE:
<223> OTHER INFORMATION: TSN17

<400> SEQUENCE: 45

Gly Ser Glu Gly Val Arg Ser Gly Arg Ser Gly
1               5                   10

<210> SEQ ID NO 46
<211> LENGTH: 14
<212> TYPE: PRT
<213> ORGANISM: Artificial Sequence
<220> FEATURE:
<223> OTHER INFORMATION: TSN18

<400> SEQUENCE: 46

Gln Pro Gln Pro Leu Pro Ser Pro Gly Val Gly Gly Lys Asn
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Tylotoin

<400> SEQUENCE: 47

```
Lys Cys Val Arg Gln Asn Asn Lys Arg Val Cys Lys
1               5                   10

<210> SEQ ID NO 48
<211> LENGTH: 10
<212> TYPE: PRT
<213> ORGANISM: Artificial Sequence
<220> FEATURE:
<223> OTHER INFORMATION: UN1

<400> SEQUENCE: 48

Glu Leu Leu Glu Ser Tyr Ile Asp Gly Arg
1               5                   10

<210> SEQ ID NO 49
<211> LENGTH: 13
<212> TYPE: PRT
<213> ORGANISM: Artificial Sequence
<220> FEATURE:
<223> OTHER INFORMATION: UN2

<400> SEQUENCE: 49

Thr Ala Thr Ser Glu Tyr Gln Thr Phe Phe Asn Pro Arg
1               5                   10

<210> SEQ ID NO 50
<211> LENGTH: 24
<212> TYPE: PRT
<213> ORGANISM: Artificial Sequence
<220> FEATURE:
<223> OTHER INFORMATION: UN3

<400> SEQUENCE: 50

Glu Leu Leu Glu Ser Tyr Ile Asp Gly Arg Pro Thr Ala Thr Ser Glu
1               5                   10                  15

Tyr Gln Thr Phe Phe Asn Pro Arg
            20

<210> SEQ ID NO 51
<211> LENGTH: 6
<212> TYPE: PRT
<213> ORGANISM: Artificial Sequence
<220> FEATURE:
<223> OTHER INFORMATION: WKYMVm
<220> FEATURE:
<221> NAME/KEY: MISC_FEATURE
<222> LOCATION: (6)..(6)
<223> OTHER INFORMATION: D-amino acid

<400> SEQUENCE: 51

Trp Lys Tyr Met Val Met
1               5
```

ANASTOMOSIS FORMATION WITH MAGNETIC DEVICES HAVING TEMPORARY RETENTION MEMBER

CROSS-REFERENCE TO RELATED APPLICATION

The present application claims priority from U.S. provisional patent application No. 63/080,363, filed on Sep. 18, 2020, and entitled "ANASTOMOSIS FORMATION WITH MAGNETIC DEVICES HAVING TEMPORARY RETENTION MEMBER", the disclosure of which is hereby incorporated by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 15,000 Byte ASCII (Text) file named "2021-11-10_Sequence_Listing_ST25" created on Nov. 10, 2021.

TECHNICAL FIELD

The technical field generally relates to medical techniques for treating digestive tract conditions. In particular, the technical field relates to medical techniques including devices for forming an anastomosis in the digestive tract.

BACKGROUND

Metabolic surgeries and medical procedures to treat conditions associated with the digestive tract, diabetes and obesity often require alteration of the digestive tract through incisions, sutures, punctures and/or stapling, which can cause trauma to the organ being altered and lead to bleeding. For instance, bariatric surgery procedures can be used to treat obesity, and can be aimed at bypassing a portion of the stomach and/or the intestine. Such medical procedures can also lead to an increased risk of infection or other complications.

Magnetic compression anastomosis can be used in the context of medical procedures to treat conditions associated with the digestive tract. With magnetic compression anastomosis, necrosis is induced in tissue sandwiched between two magnets. A healing process takes place around the magnets, while the compressed tissue eventually dies and separates from surrounding living tissue. The magnets are released along with the necrotic tissue, leaving an open passage known as an anastomosis.

There remain a number of challenges with respect to surgery procedures in the digestive tract, particularly in the formation of an anastomosis.

SUMMARY

In accordance with an aspect, there is provided a system for forming an anastomosis between two adjacent walls of a digestive tract, the system comprising:
first and second magnetic implants configured to magnetically couple to each other through the two adjacent walls of the digestive tract to compress a portion of the two adjacent walls therebetween and form a necrotic area that becomes surrounded by a scarred edge following a healing time period; and a retention member extending outwardly from a corresponding one of the first and second magnetic implants, the retention member being configured to retain the first and second magnetic implants in position and prevent passage thereof through the necrotic area during the healing time period.

In some implementations, at least one of the first and second magnetic implants comprises a housing configured to house a magnet therein.

In some implementations, the housing of the at least one of the first and second magnetic implants fully encloses the magnet therein.

In some implementations, at least one of the first and second magnetic implants comprises multiple magnets.

In some implementations, the multiple magnets are connected to each other by a cable, a string, a ribbon, a hitch, or a combination thereof.

In some implementations, the multiple magnets are housed within a single housing.

In some implementations, the single housing comprises a lumen-oriented portion and a tissue-contacting portion.

In some implementations, at least one of the first and second magnetic implants comprises a flat compression surface.

In some implementations, each one of the multiple magnets is housed within a corresponding housing.

In some implementations, the multiple magnets are interconnected to form a geometrically-shaped array once implanted in the digestive tract.

In some implementations, the geometrically-shaped array is a linear array, a circular array, or an octagonal array.

In some implementations, each of the corresponding housings comprises a flat compression surface.

In some implementations, at least one of the first and second magnetic implants comprises a connecting member connectable to a connector extending from a corresponding endoscope to be releasably engageable with the connector.

In some implementations, the connector is a delivery catheter.

In some implementations, the connecting member comprises a delivery catheter attachment assembly connectable to the delivery catheter.

In some implementations, the connecting member comprises a pommel snare or a knob.

In some implementations, the retention member comprises a flange or a series of flanges.

In some implementations, the retention member comprises a flange or a series of flanges that is integral with the housing.

In some implementations, the retention member comprises a flange or a series of flanges that is discrete from the housing.

In some implementations, the retention member comprises a continuous rim extending circumferentially around a corresponding one of the first and second magnetic implants.

In some implementations, the retention member comprises discrete arms.

In some implementations, the retention member and the housing are made of a same material.

In some implementations, the retention member and the housing are made of a different material.

In some implementations, the retention member and the housing are manufactured in a same manufacturing process.

In some implementations, the retention member and the housing are manufactured in a different manufacturing process.

In some implementations, the retention member is attachable, engageable, or couplable to the housing following the different manufacturing process.

In some implementations, the retention member comprises at least one of a bioerodible material, a biodegradable material, and a bioresorbable material.

In some implementations, the retention member comprises a synthetic aliphatic polyester.

In some implementations, the retention member comprises at least one of polylactic acid, polyglycolic acid, polylactic-co-glycolic acid, polycaprolactone, and polydioxanone.

In some implementations, the bioerodible material is a bioerodible hydrogel.

In some implementations, the retention member comprises at least two materials, the at least two materials having a different dissolution rate or a different degradation rate once implanted in a given environment.

In some implementations, the retention member comprises at least one notch or spot having a dissolution rate or a degradation rate that is different from a remainder thereof once implanted in a given environment.

In some implementations, the retention member of the first and second magnetic implants is made of a same material.

In some implementations, the retention member of the first magnetic implant is made from a different material than the retention member of the second magnetic implant.

In some implementations, the first magnetic implant is configured for implantation in a strongly acidic environment and the second magnetic implant is configured for implantation in a weakly acidic environment, and once implanted in the strong acidic environment and in the weak acidic environment respectively, the first and second retention member have a similar dissolution rate or degradation rate.

In some implementations, the retention member comprises polydimethylsiloxane or a fluoropolymer.

In some implementations, the retention member comprises a titanium alloy, cobalt chromium, or an austenitic stainless steel.

In some implementations, the retention member comprises an elastomeric material.

In some implementations, the retention member of the first magnetic implant and the retention member of the second magnetic implant have a same configuration.

In some implementations, the retention member of the first magnetic implant and the retention member of the second magnetic implant have a different configuration.

In some implementations, the retention member comprises an outwardly-extending inner surface oriented towards the tissue of the digestive tract, the outwardly-extending inner surface being substantially flat.

In some implementations, the retention member comprises an outwardly-extending inner surface oriented towards the tissue of the digestive tract, the outwardly-extending inner surface comprising a curvature.

In some implementations, the outwardly-extending inner surface has a length between about 0.5 mm and about 10 mm.

In some implementations, a gap is defined between the outwardly-extending inner surfaces of the retention members of the corresponding first and second magnetic implants once implanted in the digestive tract.

In some implementations, wherein the gap is at least 0.2 mm.

In some implementations, the retention member comprises an outwardly-extending outer surface that is continuous with a top surface of a corresponding one of the first and second magnetic implants.

In some implementations, the retention member comprises an outwardly-extending outer surface, and wherein a transition from the outwardly-extending surface to a top surface of a corresponding one of the first and second magnetic implants defines a step change.

In some implementations, the retention member is rigid.

In some implementations, the retention member is flexible.

In some implementations, the retention member is defeatable following the healing time period.

In some implementations, the retention member is defeatable mechanically using an endoscope.

In some implementations, the retention member is defeatable via a dissolution mechanism or a degradation mechanism.

In some implementations, the retention member extends outwardly from the corresponding one of the first and second magnetic implants at a right angle.

In some implementations, the retention member extends outwardly from the corresponding one of the first and second magnetic implants at an obtuse angle.

In some implementations, the retention member extends outwardly from the corresponding one of the first and second magnetic implants at an acute angle.

In some implementations, the retention member comprises a portion that is foldable against the corresponding one of the first and second magnetic implants for delivery within the digestive tract, the foldable portion being configured to unfurl once the corresponding one of the first and second magnetic implants is implanted within the digestive tract.

In some implementations, the retention member is configured to adopt a retracted configuration for delivery within the digestive tract, and an expanded configuration once a corresponding one of the first and second magnetic implants is implanted within the digestive tract.

In some implementations, the retention member comprises a self-expandable material.

In some implementations, the retention member comprises a shape-memory material

In some implementations, the retention member changes from the retracted configuration to an expended configuration following a change in temperature.

In some implementations, the shape-memory material comprises nitinol.

In some implementations, the retention member comprises a biasing mechanism.

In some implementations, the retention member comprises a layer of a drug promoting fibrosis or tissue repair.

In some implementations, the retention member comprises a lubricious coating.

In some implementations, the retention members of the first and second magnetic implants are configured such that the implant remain within the digestive tract for at least about 2 weeks or for about 2 weeks to about 4 weeks.

In some implementations, the retention member is configured such that the first and second magnetic implants are passed via manipulation of an external magnet or by an endoscopic device.

In accordance with another aspect, there is provided a system for forming an anastomosis between two adjacent walls of a digestive tract, the system comprising:

first and second magnetic implants configured to magnetically couple to each other through the two adjacent walls of the digestive tract to compress a portion of the two adjacent walls therebetween and form a necrotic area that becomes surrounded by a scarred edge following a healing time period; and a retention member extending outwardly from at least one of the first and second magnetic implants, the retention member being configured to retain the first and second magnetic implants in position and prevent passage thereof through the necrotic area during the healing time period.

In some implementations, the system further comprises one or more features as defined herein and/or described herein and/or illustrated herein.

In accordance with another aspect, there is provided a system for forming an anastomosis between two adjacent walls of a digestive tract, the system comprising:

first and second magnetic implants each comprising a tissue-contacting portion and being configured to magnetically couple to each other through the two adjacent walls of the digestive tract to compress a portion of the two adjacent walls therebetween and form a necrotic area that becomes surrounded by a scarred edge following a healing time period, the tissue-contacting portion of the first magnetic implants comprising:

a standoff feature being configured to maintain a space between respective tissue-contacting portions of the first and second magnetic implants when the standoff feature contacts the tissue-contacting portion of the second magnetic implant;

a retention member extending outwardly from a corresponding one of the first and second magnetic implants, the retention member being configured to retain the first and second magnetic implants in position and prevent passage thereof through the necrotic area during the healing time period.

In some implementations, the standoff feature includes a plurality of standoff features provided in a spaced-apart relationship.

In some implementations, the tissue-contacting portion of the second magnetic implant is substantially flat.

In some implementations, the tissue-contacting portion of the second magnetic implant comprises a recess having a shape that is complimentary to the standoff feature, the standoff feature having a higher height than a depth of the recess.

In some implementations, the standoff feature has a circular shape.

In some implementations, the standoff feature has a polygonal shape.

In some implementations, the standoff feature comprises angled sides walls.

In some implementations, the standoff feature comprises sides walls provided at a substantially right angle.

In some implementations, the standoff feature is configured to provide a focal pressure gradient therearound.

In some implementations, the system further comprises one or more features as defined herein and/or described herein and/or illustrated herein.

In accordance with another aspect, there is provided a device for forming an anastomosis between two adjacent walls of a digestive tract, the device comprising:

a first and second magnets configured to magnetically couple to each other through the two adjacent walls of the digestive tract to compress a portion of the two adjacent walls therebetween and form a necrotic area that becomes surrounded by a scarred edge following a healing time period; and a flange for retaining the pair of magnets once coupled within the digestive tract during the healing time period, the flange being couplable to a corresponding one of the first and second magnetic implants.

In some implementations, the device further comprises one or more features as defined herein and/or described herein and/or illustrated herein.

In accordance with another aspect, there is provided a system for forming an anastomosis between two adjacent walls of a digestive tract, the system comprising:

first and second magnetic implants configured to magnetically couple to each other through the two adjacent walls of the digestive tract to compress a portion of the two adjacent walls therebetween and form a necrotic area that becomes surrounded by a scarred edge following a healing time period, at least one of the first and second magnetic implants comprising:

a magnet; and a housing configured to house the magnet therein; and a retention member extending outwardly from a corresponding one of the first and second magnetic implants, the retention member being configured to retain the first and second magnetic implants in position and prevent passage thereof through the necrotic area during the healing time period;

wherein at least one of the housing and the retention member is configured to enable release of a drug therefrom once implanted in the digestive tract.

In some implementations, the retention member and the housing are made of a same material.

In some implementations, the retention member and the housing are made of a different material.

In some implementations, the material from which is made the at least one of the housing and the retention member comprises a matrix that is configured to include the drug therein up to a given timepoint once implanted in the digestive tract.

In some implementations, the matrix is configured to progressively release the drug therefrom once the at least one of the housing and the retention member is implanted in the digestive tract.

In some implementations, the matrix comprises a bioerodible material that is configured to undergo degradation once implanted in the digestive tract.

In some implementations, the bioerodible material comprises at least one of polylactic acid, polyglycolic acid and polylactic-co-glycolic acid.

In some implementations, the bioerodible material comprises polydimethylsiloxane.

In some implementations, the drug has at least one of pro-thrombosis properties, antifibrinolytic properties and wound-healing properties.

In some implementations, the drug comprises at least one of tranexamic acid, aprotinin, epsilon-aminocaproic acid, aminomethylbenzoic acid, aminocaproic acid, insulin, matrikines, and antibiotics.

In some implementations, the drug comprises a peptide.

In some implementations, the drug comprises a plurality of drugs.

In some implementations, the matrix is configured such that at least two drugs of the plurality of drugs are released therefrom sequentially.

In some implementations, the plurality of drugs comprises an antifibrinolytic drug and a wound-healing promoting drug, and the antifibrinolytic drug is released first and the wound-healing promoting drug is released second.

In some implementations, the matrix is configured such that at least two drugs of the plurality of drugs are released therefrom substantially simultaneously.

In some implementations, the system further comprises one or more features as defined herein and/or described herein and/or illustrated herein.

In accordance with another aspect, there is provided a system for forming an anastomosis between two adjacent walls of a digestive tract, the system comprising:
  first and second magnetic implants configured to magnetically couple to each other through the two adjacent walls of the digestive tract to compress a portion of the two adjacent walls therebetween and form a necrotic area that becomes surrounded by a scarred edge following a healing time period, at least one of the first and second magnetic implants comprising:
    a magnet; and
    a housing configured to house the magnet therein; and
  a retention member extending outwardly from a corresponding one of the first and second magnetic implants, the retention member being configured to retain the first and second magnetic implants in position and prevent passage thereof through the necrotic area during the healing time period.
  wherein at least one of the housing and the retention member is configured to contain a biologically active component therein.

In some implementations, the biologically active component comprises viable cells.

In some implementations, the biologically active component comprises at least one of fibroblast and stem cells.

In some implementations, the at least one of the housing and the retention member is configured to progressively release the biologically active component therefrom once implanted in the digestive tract.

In some implementations, the at least one of the housing and the retention member comprises a bioresorbable material.

In some implementations, the at least one of the housing and the retention member comprises a semi-permeable membrane.

In some implementations, the semi-permeable membrane is configured to enable diffusion of oxygen and cell nutrients.

In some implementations, the biologically active component comprises a plurality of biologically active components.

In some implementations, the wherein the at least one of the housing and the retention member is configured such that at least two biologically active components of the plurality of drugs are released therefrom sequentially.

In some implementations, the wherein the at least one of the housing and the retention member is configured such that at least two drugs of the plurality of biologically active components are released therefrom substantially simultaneously.

In some implementations, the system further comprises one or more features as defined herein and/or described herein and/or illustrated herein.

In accordance with another aspect, there is provided a method for forming an anastomosis between two adjacent walls of a digestive tract of a patient, the method comprising:
  navigating a first magnetic implant into the digestive tract to a first location on one side of a desired anastomose site;
  delivering a second magnetic implant into the digestive tract to a second location on another side of the desired anastomose site;
  magnetically coupling the first and second magnetic implants to each other through the two adjacent vessel walls of the digestive tract to compress a portion of the two adjacent walls therebetween and form a necrotic area; and
  retaining the first and second magnetic implants in position on respective sides of the two adjacent walls during a healing time period to enable formation of a scarred edge that surrounds the necrotic area.

In some implementations, navigating the first magnetic implant comprises releasably engaging the first and second magnetic implants with a corresponding delivery catheter insertable in a working channel of a corresponding endoscope via a connecting member.

In some implementations, the method further comprises mechanically defeating the retention member using an endoscope following the healing time period.

In some implementations, the method further comprises passing at least one of the first and second magnetic implants via the bowel lumen by manipulating a magnet externally or by manipulating an endoscopic device internally.

In some implementations, retaining the first and second magnetic implants in position on respective sides of the two adjacent walls comprises providing a retention member extending outwardly from each one of the first and second magnetic implants to prevent passage thereof through the necrotic area.

In accordance with another aspect, there is provided a method for forming an anastomosis between two adjacent walls of a digestive tract of a patient, the method comprising:
  magnetically coupling a first and second magnetic implants to each other through the two adjacent vessel walls of the digestive tract to compress a portion of the two adjacent walls therebetween and form a necrotic area, each one of the first and second magnetic implants comprising a flange extending outwardly therefrom;
  holding the first and second magnetic implants in position on respective sides of the two adjacent walls during a healing time period to enable formation of a scarred edge that surrounds the necrotic area during which the flange of each one of the first and second magnetic implants prevents passage thereof through the necrotic area.

In accordance with another aspect, there is provided a system for forming an anastomosis between two adjacent walls of a digestive tract, the system comprising:
  first and second elongated magnetic implants configured to magnetically couple to each other through the two adjacent walls of the digestive tract to compress a portion of the two adjacent walls therebetween and form a necrotic area that becomes surrounded by a scarred edge following a healing time period; and
  a retention member extending outwardly from at least one of the first and second elongated magnetic implants, the retention member being configured to retain the first and second elongated magnetic implants in position and prevent passage thereof through the necrotic area during the healing time period.

In some implementations, the at least one of the first and second elongated magnetic implants comprises a housing configured to house a magnet therein.

In some implementations, the retention member comprises a flange or a series of flanges.

In some implementations, the flange extends continuously around substantially an entire periphery of the at least one of the first and second elongated magnetic implants.

In some implementations, the retention member comprises a flange or a series of flanges that is integral with the housing.

In some implementations, the retention member comprises a flange or a series of flanges that is discrete from the housing.

In some implementations, the retention member comprises a series of flanges extending around a periphery of the at least one of the first and second elongated magnetic implants, the flanges being provided in a spaced-apart relationship relative to one another.

In some implementations, the retention member comprises a continuous rim extending circumferentially around the at least one of the first and second elongated magnetic implants.

In some implementations, the retention member has a T-shaped cross-section.

In some implementations, the retention member and the housing are made of a same material.

In some implementations, the retention member and the housing are made of a different material.

In some implementations, the retention member comprises at least one of a bioerodible material, a biodegradable material, and a bioresorbable material.

In some implementations, the retention member comprises at least two materials, the at least two materials having a different dissolution rate or a different degradation rate once implanted in a given environment.

In some implementations, the retention member comprises at least one notch or spot having a dissolution rate or a degradation rate that is different from a remainder thereof once implanted in a given environment.

In some implementations, each one of the first and second elongated magnetic implants comprises a corresponding retention member extending outwardly therefrom, the corresponding retention member of the first and second elongated magnetic implants being made of a same material.

In some implementations, each one of the first and second elongated magnetic implants comprises a corresponding retention member extending outwardly therefrom, the corresponding retention member of the first magnetic implant being made from a different material than the corresponding retention member of the second magnetic implant.

In some implementations, the first elongated magnetic implant is configured for implantation in a strongly acidic environment and the second elongated magnetic implant is configured for implantation in a weakly acidic environment, and once implanted in the strongly acidic environment and in the weak acidic environment respectively, the first and second elongated retention member have a similar dissolution rate or degradation rate.

In some implementations, the retention member comprises an outwardly-extending inner surface oriented towards the tissue of the digestive tract, the outwardly-extending inner surface being substantially flat.

In some implementations, the retention member comprises an outwardly-extending inner surface oriented towards the tissue of the digestive tract, the outwardly-extending inner surface comprising a curvature.

In some implementations, each one of the first and second elongated magnetic implants comprises a corresponding retention member extending outwardly therefrom, each one of the corresponding retention members comprising an outwardly-extending inner surface oriented towards the tissue of the digestive tract, a gap being defined between the outwardly-extending inner surfaces of the corresponding retention members of the first and second elongated magnetic implants once implanted in the digestive tract.

In some implementations, the retention member comprises a portion that is foldable against the at least one of the first and second elongated magnetic implants for delivery within the digestive tract, the foldable portion being configured to unfurl once the at least one of the first and second elongated magnetic implants is implanted within the digestive tract.

In some implementations, the retention member is configured to adopt a retracted configuration for delivery within the digestive tract, and an expanded configuration once the at least one of the first and second elongated magnetic implants is implanted within the digestive tract.

In accordance with another aspect, there is provided a system for forming an anastomosis between two adjacent walls of a digestive tract, the system comprising:

first and second elongated magnetic implants each comprising a tissue-contacting portion and being configured to magnetically couple to each other through the two adjacent walls of the digestive tract to compress a portion of the two adjacent walls therebetween and form a necrotic area that becomes surrounded by a scarred edge following a healing time period, the tissue-contacting portion of the first elongated magnetic implant comprising:

a standoff feature being configured to maintain a space between respective tissue-contacting portions of the first and second elongated magnetic implants when the standoff feature contacts the tissue-contacting portion of the second elongated magnetic implant;

a retention member extending outwardly from at least one of the first and second elongated magnetic implants, the retention member being configured to retain the first and second elongated magnetic implants in position and prevent passage thereof through the necrotic area during the healing time period.

In some implementations, the standoff feature includes a plurality of standoff features provided in a spaced-apart relationship.

In some implementations, the tissue-contacting portion of the second elongated magnetic implant is substantially flat.

In some implementations, the tissue-contacting portion of the second elongated magnetic implant comprises a recess having a shape that is complimentary to the standoff feature, the standoff feature having a higher height than a depth of the recess.

In some implementations, the standoff feature comprises angled sides walls.

In some implementations, the standoff feature comprises sides walls provided at a substantially right angle.

In some implementations, the standoff feature is configured to provide a focal pressure gradient therearound.

BRIEF DESCRIPTION OF THE DRAWINGS

The attached figures illustrate various features, aspects and implementations of the technology described herein.

FIG. 4A is a perspective view of a magnetic implant and of a retention member, in accordance with an implementation.

FIG. 4B is a side view of the magnetic implant of FIG. 4A.

FIGS. 9A-9C are side views of a magnetic implant that includes multiple magnets provided in series and in an adjacent relationship and connected by a cable that is manipulated to yield an annular shape.

FIGS. 11A-11D are side views of a magnetic implant that includes multiple magnets provided in a first configuration wherein two layers of magnets are in a side-by-side relationship, and in a second configuration wherein the two layers of magnets are spaced-apart.

FIG. 18 is a side view of a magnetic implant and of a retention member that includes thinner portions, in accordance with another implementation.

FIG. 19 is a side view of a magnetic implant and of a retention member having an outwardly-extending inner surface that contacts an outer surface of a vessel of a hollow organ, in accordance with another implementation.

DETAILED DESCRIPTION

Figure 1:
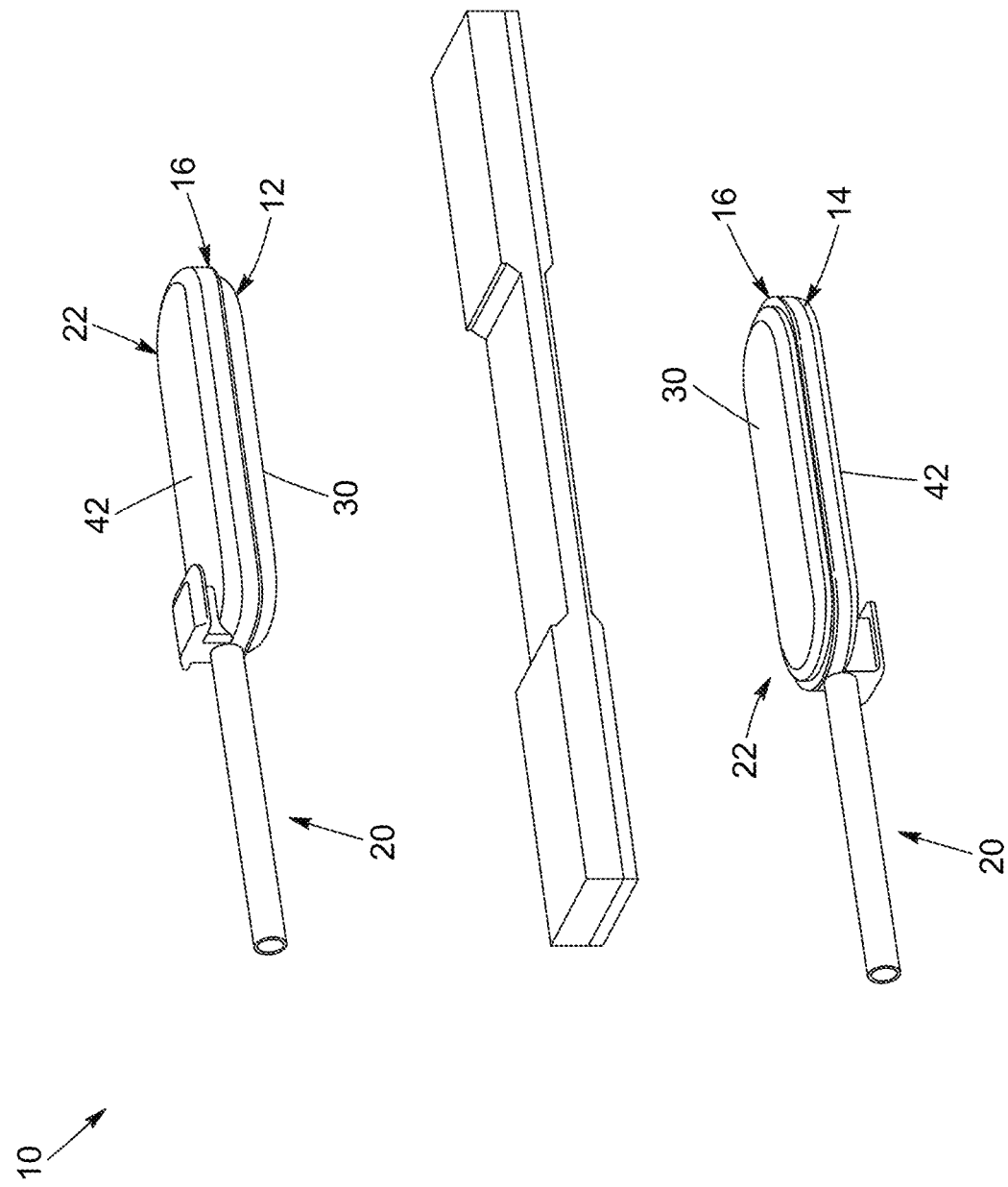
FIG. 1 is an exploded perspective view of a first magnetic implant shown on one side of a desired site of an anastomosis and of a second magnetic implant shown on another side of the desired site of the anastomosis, with a vessel wall of a first hollow organ and a vessel wall of a second hollow organ being shown therebetween, in accordance with an implementation.
Figure 2:
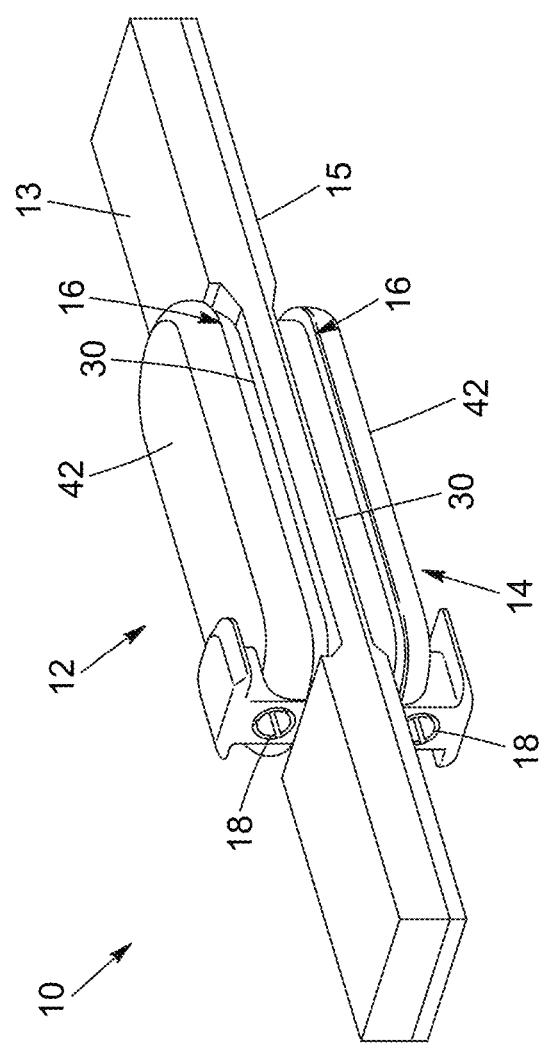
FIG. 2 is a perspective view of the first and second magnetic implants shown in FIG. 1, with the first magnetic implant being shown in contact with the vessel wall of the first hollow organ and the second magnetic implant being shown in contact with the vessel wall of the second hollow organ, at the desired site of the anastomosis.
Figure 3:
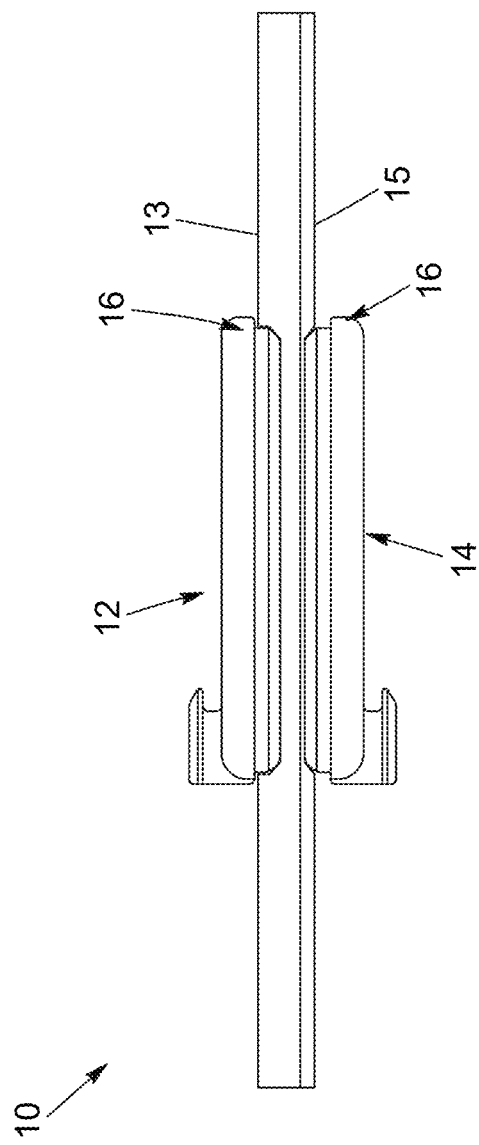
FIG. 3 is a side view of the first and second magnetic implants shown in FIG. 2.

Techniques described herein relate to systems, devices and methods for forming an anastomosis between two adjacent walls of hollow structures of the digestive tract of a patient, in the context of procedures to treat various medical conditions associated with the digestive tract. The formation of the anastomosis can be achieved without puncturing the tissue of the hollow structures through which the anastomosis is formed, for example by inserting a first magnetic implant into the lumen of a first hollow organ and a second magnetic implant into the lumen of a second hollow organ, positioning the first and second magnetic implants at a desired anastomosis site, and by magnetically coupling the first and second magnetic implants together to compress the tissue of the adjacent walls therebetween. Compression of the wall tissue between the two magnetic implants results in a necrotic area that corresponds approximately to the surface area of the compression surface of the magnetic implant pair. Over time, the necrotic area becomes surrounded by an edge of scar tissue, or scarred edge. The formation of scar tissue can include collagen fiber deposition, neovascularization, and epithelial regeneration, and represents a dynamic equilibrium involving cells, their milieu, and the extracellular matrix. Cytokines secreted by platelets and inflammatory cells can promote the formation of new blood vessels and collagen synthesis which, in dynamic balance with collagen degradation, can contribute to determine the healing response. Two components of collagen are hydroxyproline and hydroxylysine, with hydroxyproline being synthesized under conditions of oxidative stress via the hydroxylation of proline, and being involved in the cellular transport of collagen. The synthesis and transport of wound collagen can thus be understood by monitoring the hydroxyproline content of the wound. The edge of scar tissue can thus be characterized by the fusion, or mechanical bonding, of the walls of each hollow organ through which the anastomosis is formed that occurs in part via fibrosis mechanisms. The scarred edge can thus form a fluid-tight seal around the anastomosis.

To facilitate maintaining the pair of magnetic implants in place for a sufficient period of time to enable formation of the scarred edge and prevent premature passage of the pair of magnetic implants through the necrotic area, a retention member can be associated with at least one of the magnetic implants, the retention member being configured to extend outwardly from the corresponding magnetic implant. The retention member can be any temporary or permanent structure that is coupled to the magnetic implant or that forms part of the magnetic implant, and is configured to prevent or inhibit the pair of magnetic implants from prematurely passing through the necrotic area, i.e., prior to an edge healing time period being completed, such that the magnetic implants and necrotic tissue are released only after good scar formation is complete. For example, the retention member can include a flange or extension, provided continuously or discontinuously around the periphery of the magnetic implant. The retention member can also take several other forms and can include various features, for instance with regard to the materials of which the retention member is made, geometric characteristics, configurations, and so on. One of the magnetic implants, or each of the magnetic implants, can be associated with a corresponding retention member such that the magnetically coupled pair of implants is prevented from passing through the necrotic region in both directions.

Various implementations and features of the magnetic implant and associated retention member will now be described in greater detail in the following paragraphs.

General Description of the System for Forming an Anastomosis

With reference to FIGS. 1 to 6, a system 10 for forming an anastomosis between two adjacent walls of hollow organs of the digestive tract is shown. Referring more particularly to FIG. 1, in the implementation shown, the system 10 includes a first magnetic implant 12 for implantation in the stomach, the first magnetic implant 12 being identified as a "stomach implant"; and a second magnetic implant 14 for implantation in the jejunum, the second magnetic implant 14 being identified as a "jejunum implant". It is to be understood that the term "implant" refers to a device that is implanted in the digestive tract for a certain period of time, e.g., the healing time period, and that it can be used interchangeably with the term "device" or "component" for instance. In this implementation, the stomach represents a first hollow organ of the digestive tract into which the first magnetic implant 12 can be implanted, and the jejunum represents a second hollow organ into which the second magnetic implant 14 can be implanted, so as to compress a portion of the stomach wall 13 and a portion of the jejunum wall 15 therebetween.

Figure 5:
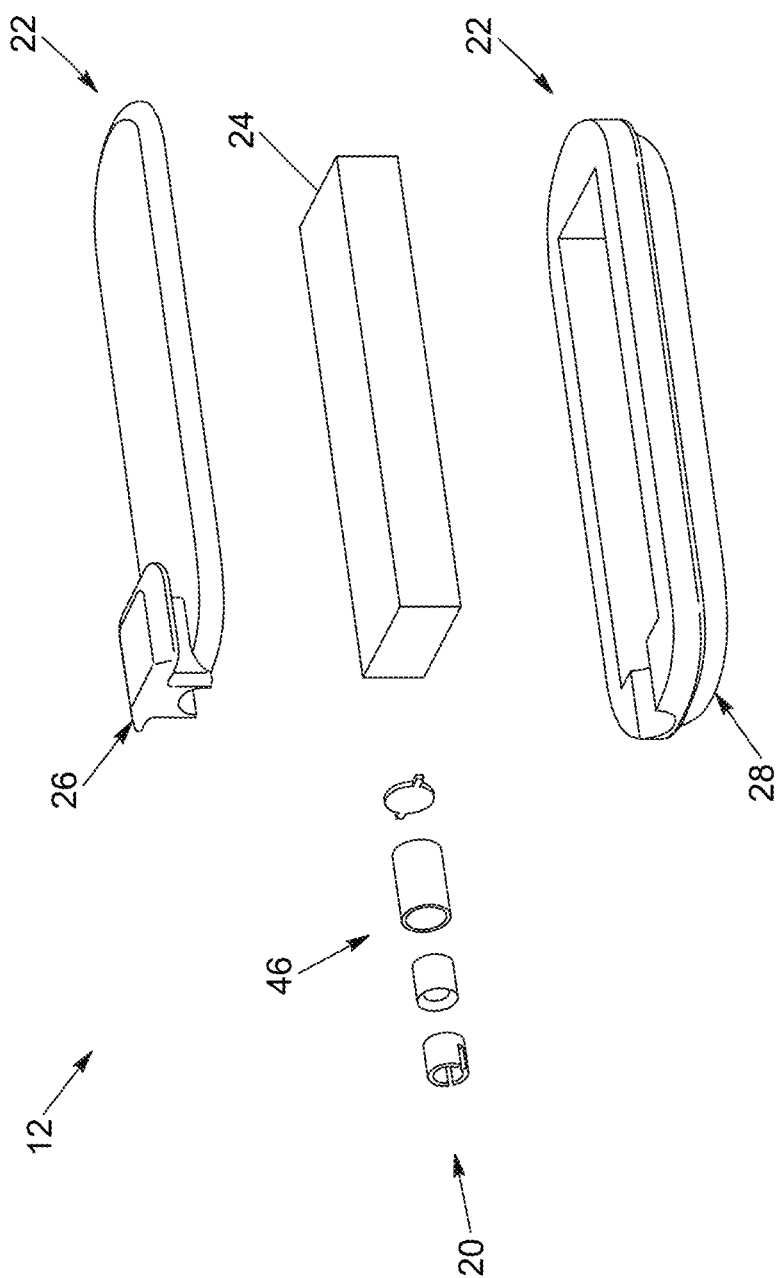
FIG. 5 is an exploded view of the magnetic implant of FIG. 4A.
Figure 6:
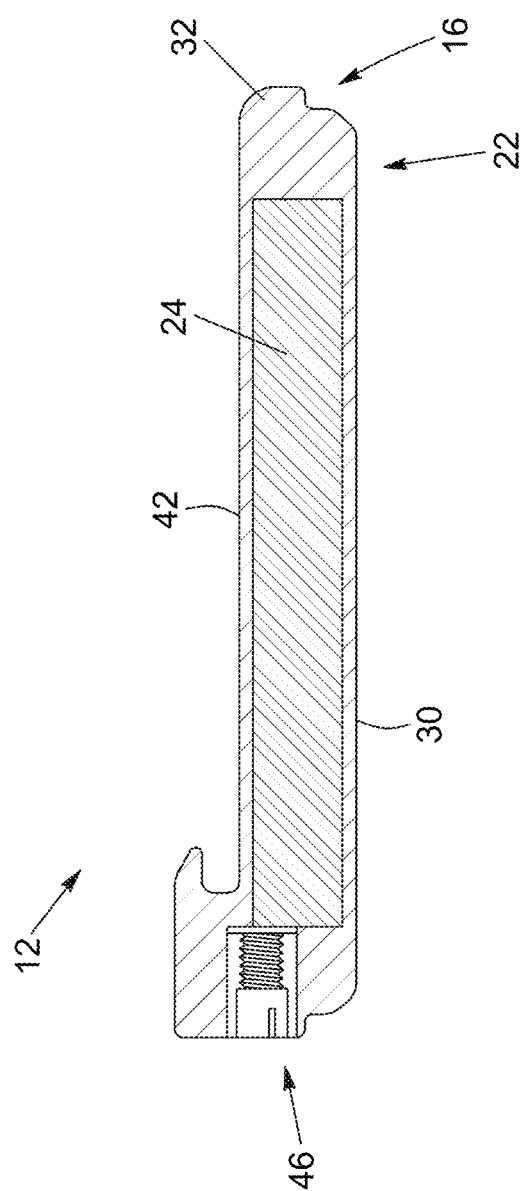
FIG. 6 is a cross-sectional view of the magnetic implant of FIG. 4A.

In the Figures, each one of the first magnetic implant 12 and the second magnetic implant 14 is associated with a retention member 16, which is illustrated as corresponding to a flange 32 in FIG. 6. In the implementation shown, each one of the first magnetic implant 12 and the second magnetic implant 14 also includes a connecting member 18 that can be releasably engageable with a connector 20, which in FIG. 1 is identified as a delivery catheter. In other words, the magnetic implant 12, 14 can include a feature that enables its connection to a connector 20 for navigating the magnetic implant 12, 14 to a desired site for creating the anastomosis. In turn, the connecting member 18 can include any feature that enables a releasable connection of the magnetic implant 12, 14 with the connector 20. In FIGS. 1-6, the connecting member 18 is shown as a "catheter attachment" that includes a catheter attachment assembly 46. The catheter attachment is configured as a receiving cavity that can receive a distal end of the connector 20 therein, which as mentioned above can be a delivery catheter.

In some implementations and as shown in FIGS. 1-6, the magnetic implant 12, 14 can include a housing 22 that encloses a magnet 24 therein. The housing 22 can include for instance an outward portion 26 (or "outward housing" in FIG. 5) and an inward portion 28 (or "inward housing" in FIG. 5). The inward housing includes the portion of the housing that faces the corresponding other magnetic implant and is involved in the magnetic compression of the tissue, while the outward housing is on the opposed side of the magnetic implant facing away from the tissue being compressed. In this example, the two housing components surround the magnet and can be coupled together around a periphery thereof. Other housing constructions are also possible, where one or more housing components are used to partly or fully enclose the magnet.

Each of these components of the system for forming an anastomosis will now be described in further detail.

Description of the Magnetic Implant

Still referring to FIGS. 1-6, the first magnetic implant 12 is a device that is implantable into a first hollow organ of the digestive tract of a patient at a site of a desired anastomosis via the lumen of the first hollow organ. Examples of hollow organs of the digestive tract include the oesophagus, stomach, duodenum, jejunum, ileum, colon, biliary tract, and pancreatic duct. A site of desired anastomosis can be determined according to the condition of the patient, and this aspect will not be discussed further in the context of the present description. As used herein, the expression "magnetic implant" refers to a structure that can be implanted into the chosen hollow organ of the digestive tract, and that can be magnetically attracted to another magnetic implant due to magnetic forces. In some implementations, the magnetic implant can consist of a magnet. In some implementations, the magnetic implant can include a magnet and one or more additional features, such as a housing and/or a connecting member. The two magnetic implants can be substantially the same as each other, or different, in terms of their shape, configuration, construction, and/or material make-up. These features will be further discussed below.

The first magnetic implant 12 is used with a second magnetic implant 14 to form am implant pair. The second magnetic implant 14 is a device implantable into a second hollow organ of the digestive tract of the patient to the site of the desired anastomosis via the lumen of the second hollow organ. The second hollow organ of the digestive tract is located in sufficiently close proximity of the first hollow organ to enable the convergence of the respective wall tissue of the first hollow organ and the second hollow organ to eventually form the anastomosis.

The first and second magnetic implants 12, 14 are configured to remain within the digestive tract for at least a given healing time period. The healing time period enables necrosis of the anastomosis area while providing enough time for the edge of scar tissue to form. In some implementations, after approximately 3 to 5 days following implantation of the pair of magnetic implants at the desired site of the anastomosis, the periphery of the anastomosis is strengthened by collagen deposition, with the formation an edge of scar tissue having an increased tensile strength occurring at an estimated of approximately 7 to 10 days following implantation. The duration for forming the scar tissue can vary depending on the overall health of the individual patient, and depending on the specific parts of the digestive tract being joined. The scar tissue can also gain strength over the course of several additional weeks. In some implementations, it may be desirable for the magnetic implants to be released and passed out of the body of the patient about two weeks after implantation. In some implementations, the healing time period can be about two weeks, or at least two weeks.

Each one of the first and second magnetic implants 12 can be navigated to the site of the desired anastomosis using various techniques. For instance, the magnetic implants 12, 14 can be delivered to the site of the desired anastomosis endoscopically.

Each one of the first and second magnetic implants 12, 14 can have any suitable shape and size determined in accordance with their intended purpose. In some implementations, the size and the shape of the magnetic implant can be determined for instance in accordance with the characteristics of the site of the desired anastomosis, the delivery technique chosen to deliver the magnetic implant to the site of the desired anastomosis, and so on. In some implementations, the magnetic implant can have for example an elliptic shape, a circular shape, an elongated shape, a rectangular shape, an octagonal shape, or any other polygonal shape in terms of its cross-section. The magnetic implant can include rounded corners to facilitate navigation into the digestive tract. The magnetic implant can have an aspect ratio of about 1:1 (e.g., in the case of a circular cross-section) or an aspect ratio of about 1:2 to 1:40, about 1:3 to 1:20, about 1:4 to 1:15, for example, or another aspect ratio. In some implementations, the shape and size of the retention member 16 can be adapted in accordance with the shape and size of the corresponding magnetic implant. For instance, in some implementations, the height of the magnetic implant can be proportional to the thickness of the magnet contained therein and hence desired magnetic strength.

Each of the first and second magnetic implants 12, 14 includes a compression surface 30 that is configured to contact the tissue of the corresponding hollow organ. The compression surface 30 can also be referred to as a tissue-contacting surface, since it is the surface of the magnetic implant that is eventually in contact with the interior wall of the hollow organ once the magnetic implant is delivered to the site of the desired anastomosis. Each of the first and second magnetic implants 12, 14 also includes a lumen-oriented surface 42 opposite the tissue-contacting surface, the lumen-oriented surface generally facing the lumen of the hollow organ once the magnetic implant is delivered to the site of the desired anastomosis.

Figure 7:
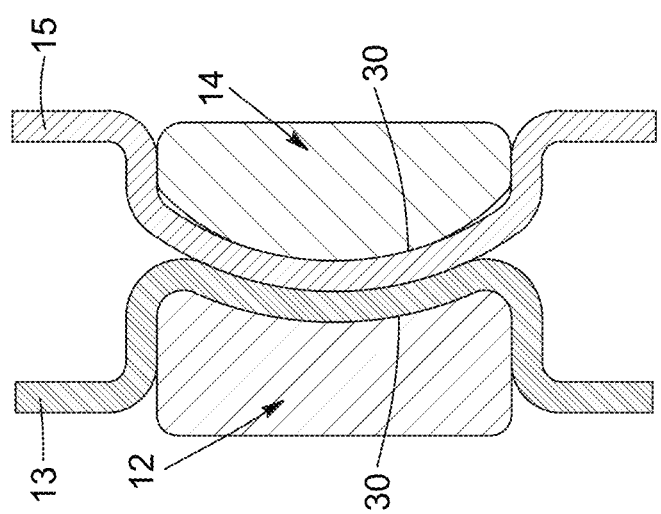
FIG. 7 is a cross-sectional view of a first magnetic implant shown on one side of a desired site of an anastomosis and of a second magnetic implant shown on another side of the desired site of the anastomosis, with a vessel wall of a first hollow organ and a vessel wall of a second hollow organ being shown therebetween, the first magnetic implant including a compression surface that is inwardly curved and the second magnetic implant including a compression surface that is outwardly curved.

In some implementations, the compression surface 30 can be substantially continuous and flat, as shown in FIGS. 1-6. This can contribute to evenly distribute the force of the magnetic implant onto the tissue once the first and second magnetic implants 12, 14 are magnetically coupled together. In other implementations and with reference to FIG. 7, the compression surface 30 of the first magnetic implant 12 can have a complementary shape compared to the compression surface 30 of the second magnetic implant 14. In the implementation shown in FIG. 7, the first magnetic implant 12 has a curvilinear surface that is inwardly curved, i.e., concave, and the second magnetic implant 14 has a complimentary curvilinear surface that is outwardly curved, i.e., convex, for the first magnetic implant 12 to mate therewith.

In other implementations, the compression surface 30 can include features such as ridges, crests, furrows, grooves, and the like. For instance, the compression surface 30 of the first magnetic implant 12 can include a series of ridges, and the second magnetic implant 14 can include a complimentary series of furrows such that when the first and second magnetic implants 12, 14 are magnetically coupled, the first and second magnetic implants 12, 14 can interlock and/or self-align to increase the stability of their positioning on their respective sides of the first and second hollow organs. In some implementations, only one of the magnetic implants can include a compression surface having a convex feature, as will be discussed in further detail below.

Figure 25:
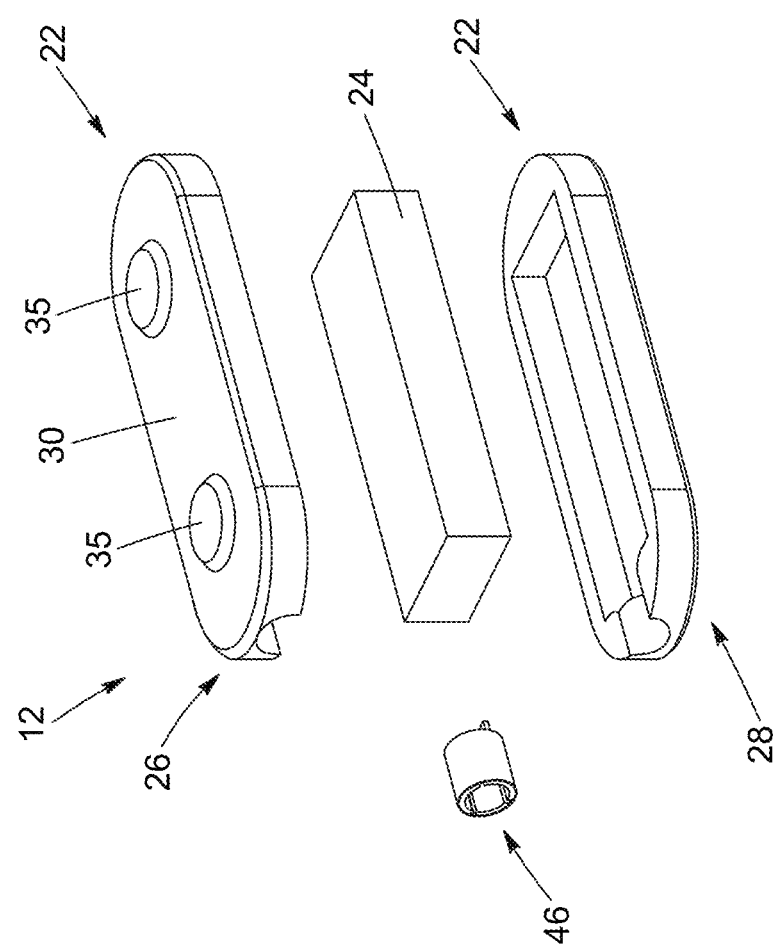
FIG. 25 is an exploded view of a magnetic implant having a compression surface that includes two standoff features, in accordance with an implementation.
Figure 26:
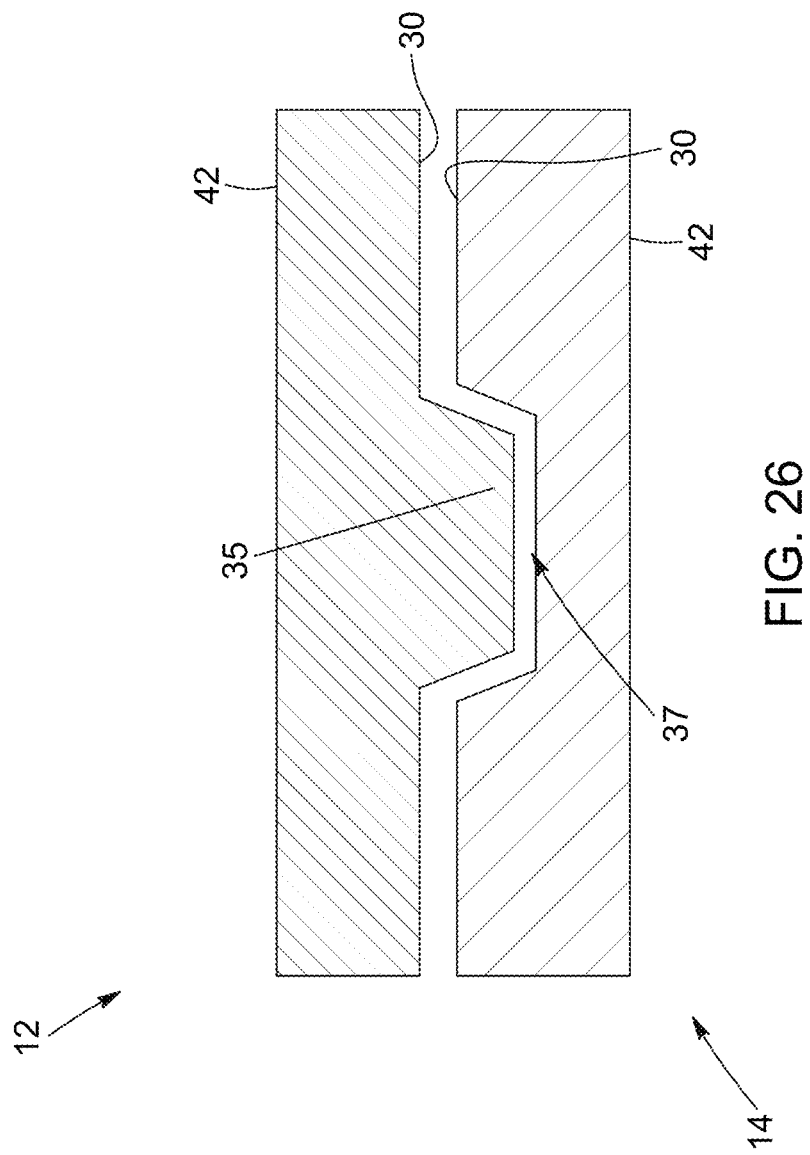
FIG. 26 is a cross-sectional view of first and second magnetic implants, the first magnetic implant having a compression surface that includes a standoff feature configured to mate with a corresponding recess defined in a compression surface of the second magnetic implant, in accordance with an implementation.
Figure 29:
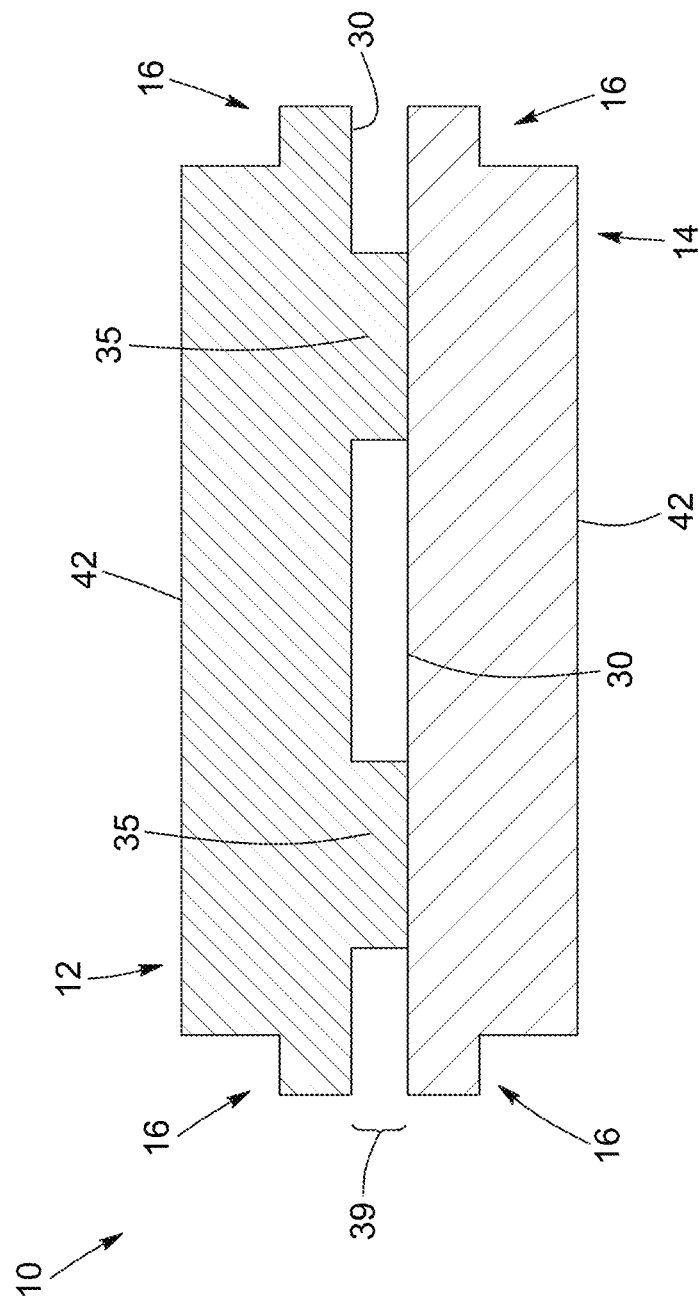
FIG. 29 is a cross-sectional view of first and second magnetic implants and corresponding retention members, the first magnetic implant having a compression surface that includes two standoff features, in accordance with another implementation.

With reference to FIGS. 25 and 26, in the embodiment shown, the compression surface 30 of a first magnetic implant 12 includes two standoff features 35 provided in a spaced-apart relationship. In the embodiment shown, the standoff features 35 are each represented as a convex structure extending outwardly from the remainder of the compression surface 30. In some implementations, the standoff feature 35 can be configured to mate with a corresponding recess 37 defined in the compression surface 30 of a second magnetic implant 14, such as shown in FIG. 26. In some implementations and as mentioned above, complimentary features such as a combination of one or more standoffs and corresponding recesses provided on respective compression surfaces 30 of the magnetic implants 12, 14 can contribute to provide a certain degree of stability to the magnetic implants 12, 14 once implanted in the digestive tract by limiting their range of motion in at least one direction. In other implementations, the standoff feature 35 can be configured to abut a substantially plane surface of the compression surface 30 of a second magnetic implant 14, such as shown in FIG. 29.

Figure 28:
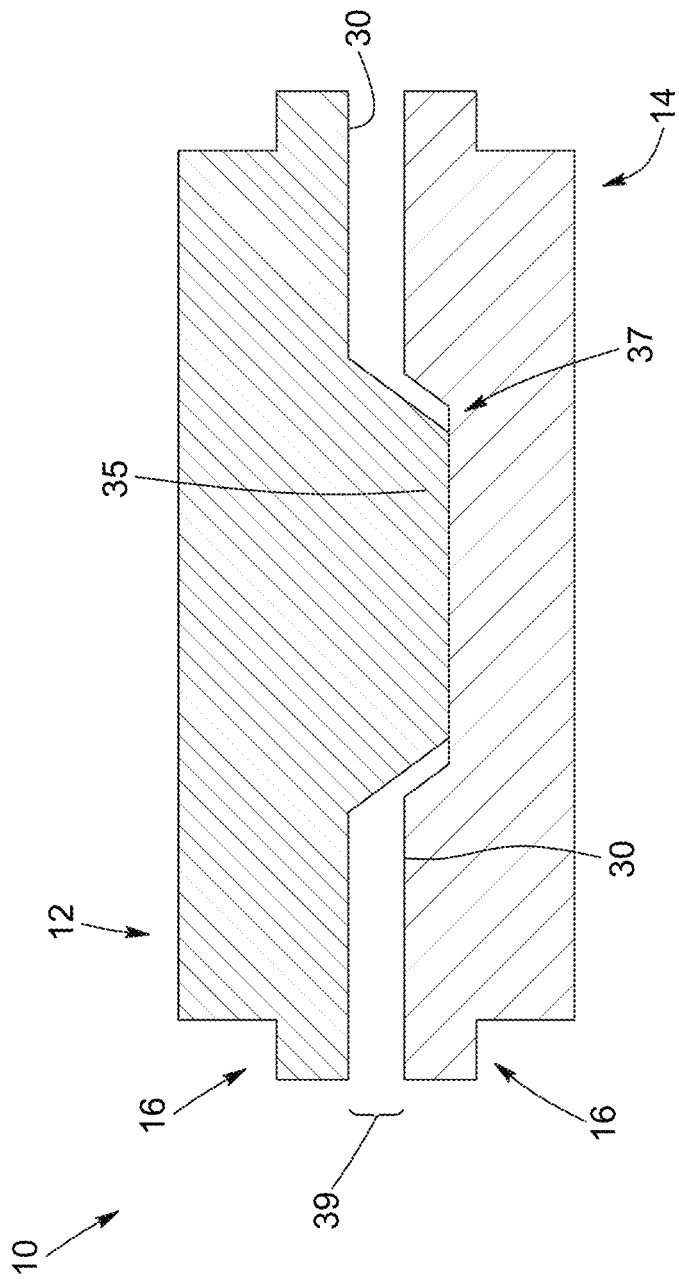
FIG. 28 is a cross-sectional view of first and second magnetic implants and corresponding retention members, the first magnetic implant having a compression surface that includes a standoff feature configured to mate with a corresponding recess defined in a compression surface of the second magnetic implant, in accordance with another implementation.

In some implementations, the size, and more particularly the height of the standoff feature 35 can be determined so as to limit the distance between the magnetic implants 12, 14 to set a maximum allowable compression of the tissues. For instance, when the standoff feature 35 has a height that is higher than the depth of the corresponding recess 37, the top surface of the standoff feature 35 can abut the bottom surface of the recess 37 such that a space 39 remains between the remainder of the respective compression surfaces of the magnetic implants, such as shown in FIG. 28. In other implementations and as illustrated in FIG. 29, when the compression surface 30 of a first magnetic implant 12 includes one or more standoff features 35 while the compression surface 30 of a second magnetic implant 14 is substantially flat, the positioning of the compression surfaces against each other can also result in a space 39 being defined between the remainder of the respective compression surfaces 30 of the magnetic implants 12, 14.

In some implementations, the standoff feature 35 can be of a size which is smaller than the overall compression footprint, which can result in a focal pressure gradient around the standoff feature 35. The presence of a focal pressure gradient can enable the tissue compressed by the standoff feature 35 to necrose at a faster rate compared to the surrounding magnetic compression area. In such implementations, a region of "regular compression" can surround the standoff feature 35, which can contribute to seal the region that is subjected to faster necrosis underneath the standoff feature 35 from leaking.

In some implementations, the standoff feature 35 can contribute to increasing the amount of shear force required to pull the magnetic implants 12, 14 apart or to slide the magnetic implants 12, 14 relative to one another.

As mentioned above, the size and shape of the standoff feature 35 can vary. For instance, the standoff feature 35 can have any suitable geometrical shape, e.g., circular, rectangular, or polygon-shaped. The standoff feature 35 can be provided with angled sides walls, such as shown in FIG. 28, or with sides walls provided at a substantially right angle, such as shown in FIG. 29. The number of standoff features 35 can also vary, and can range for instance from one to ten. More than ten standoff features 35 can also be provided, in accordance with the intended application, and depending on the size of the compression surface 30. In some implementations, the number, shape and size of the standoff features 35 can be determined in accordance with the size and shape of the surrounding magnetic compression area of the magnetic implant. For instance, in some implementations, a magnetic implant having a larger compression surface can include a higher number of standoffs features compared to a magnetic implant having a smaller compression surface.

In some implementations, the number, shape and size of the standoff features 35 can be determined so as to facilitate increasing shear strength between the first and second magnetic implants 12, 14 to prevent disconnection of the first and second magnetic implants 12, 14.

In some implementations, the standoff feature 35 can be formed of a bioresorbable material so that the magnetic force and pressure on the tissues may be limited for a given period of time, e.g., while the scar tissue forms around the perimeter of the compression surface 30. Then, as the standoff feature 35 is subjected to bioresorption, the magnetic strength and hence pressure between the magnetic implants 12, 14 can increase due to dissolution of the limiter, i.e., of the standoff feature 35.

Figure 8:
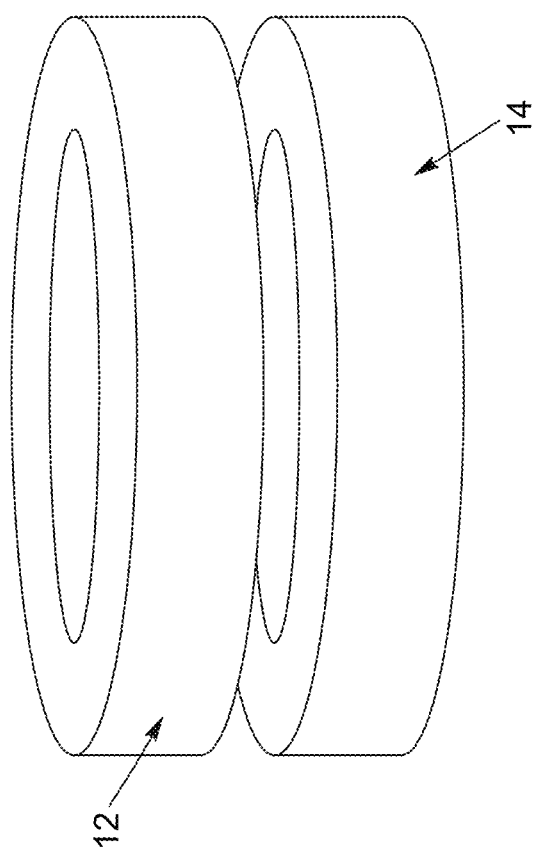
FIG. 8 is a perspective view of first and second magnetic implants having an annular shape, in accordance with an implementation.
Figure 10B:
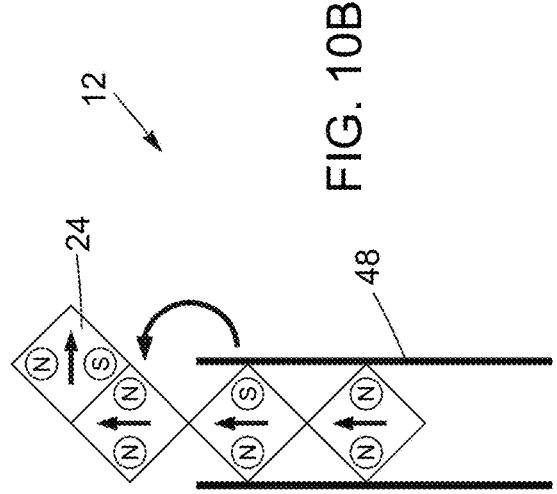
FIGS. 10A-10D are side views of a magnetic implant that includes multiple magnets, the magnetic implant unfolding to form a polygonal shape without a void space.
Figure 10D:
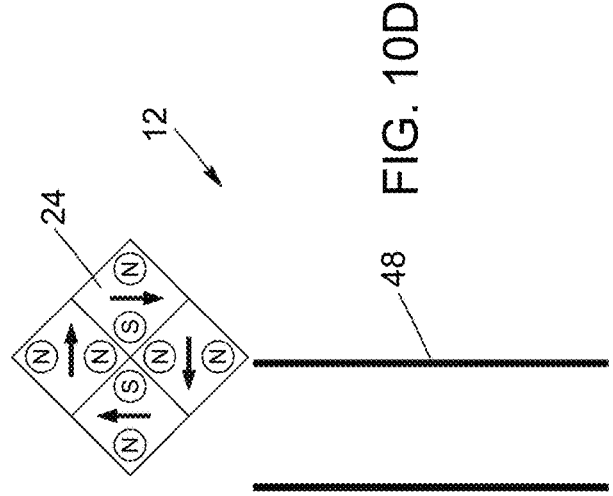
Figure 10A:
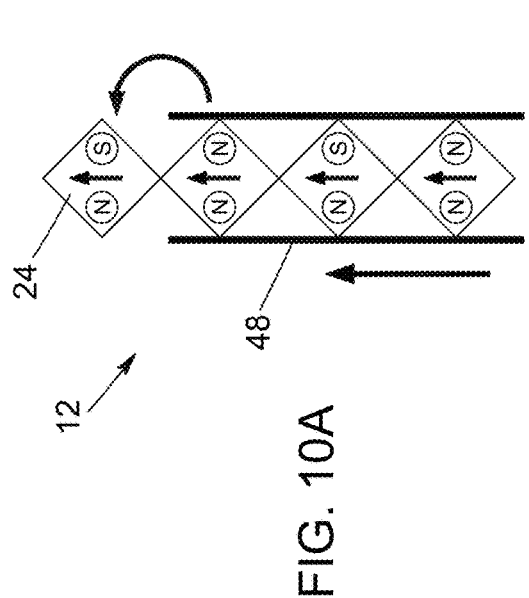
Figure 10C:
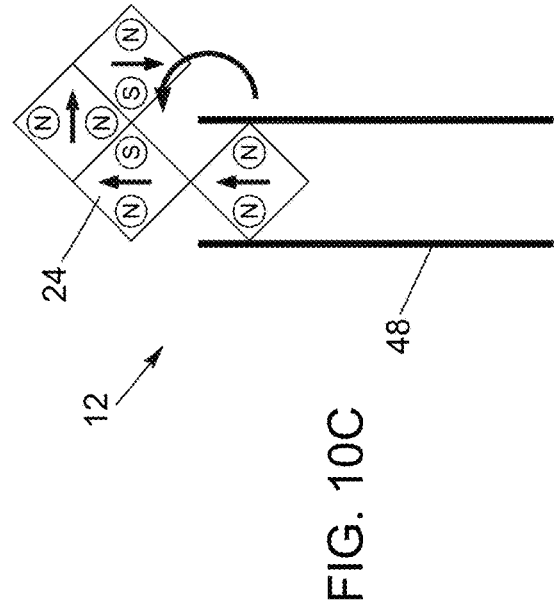

In yet other implementations, the compression surface 30 can be discontinuous and include void portions, i.e., where the wall tissue is not contacted by a portion of the magnetic implant. For instance, with reference to FIG. 8, the first and second magnetic implants 12, 14 and/or the compression surfaces 30 thereof can have a donut shape, or annular shape. In some implementations, the first and second magnetic implants 12, 14 can have a similar size and a similar or complimentary shape to facilitate the magnetic coupling through the wall tissues of the hollow organs. In other implementations, the first and second magnetic implants can 12, 14 can have a different size and shape depending on the application and the sought-after characteristics of the resulting anastomosis.

In some implementations, the magnetic implant 12, 14 can include one or more magnets. The magnet 24 can be any type of suitable magnet composed of the appropriate material. In some implementations, the magnet 24 can be chosen according to its attractive force, i.e., according to the pressure that will be exerted on the surface area of the tissue that will eventually be compressed between the first and second magnetic implants 12, 14. Factors influencing the attractive force of the magnet 24 can include the shape of the magnet 24, the thickness of the magnet 24, the material of which the magnet 24 is made, etc. Example materials include neodymium magnets (e.g., NdFeB magnets), rare earth magnets, and ferrite magnets.

In some implementations, the magnet or magnets of a first magnetic implant may be made of a magnetic material that is not permanently magnetized, such as soft magnetic alloys, e.g., nickel-iron, silicon iron, iron, iron-cobalt, and ferritic stainless steels. In other words, the magnet(s) of respective magnetic implants may not be constructed of two permanent magnets. In other implementations, the magnets of a first and second magnetic implants may be constructed of two permanent magnets.

When the magnetic implant includes multiple magnets 24, the magnets 24 can be connected to each other by a cable, a string, a ribbon, a hitch, or a combination thereof. For example, and with reference to FIGS. 9A-9C, the magnetic implant can include multiple magnets provided in series and in an adjacent relationship, the multiple magnets being connected together using a cable 76 that can be manipulated to yield an annular shape. Such a string of magnets can enable the magnetic implant to adopt a first configuration wherein the multiple magnets are provided substantially linearly to facilitate their navigation within the lumen of the hollow organ, and a second configuration wherein the multiple magnets can take the form that the magnetic implant will have once implanted at the site of the desired anastomosis, which can by any geometrical form. In the implementation shown in FIGS. 9A-9C, the form of the magnetic implant in the second configuration is an annular shape, but in other implementations, the multiple magnets can take other forms, and be for instance folded to obtain a polygonal shape without the void space, such as shown in FIGS. 10A-10D. With reference to FIGS. 11A-11D, the multiple magnets can also be provided in a first configuration wherein two layers of magnets are in a side-by-side relationship to facilitate their navigation within the lumen of the hollow organ, and then in a second configuration wherein the two layers of magnets become spaced-apart, for instance due to the repulsive force of the magnets. As mentioned above, the first configuration of the multiple magnets can generally be a configuration that facilitates their navigation within the lumen of the hollow organ, which can entail that the magnetic implant can adopt a configuration that enables it to fit within a working channel of an endoscope, or alternatively that is connectable to a distal end of an endoscope, for instance via a delivery catheter. The multiple magnets can thus be interconnected in any suitable manner that subsequently enables the formation of a geometrically-shaped array once implanted in the digestive tract, such as a linear array, a circular array, or an octagonal array.

Although not explicitly shown in FIGS. 7-11 and 20-24, it is to be understood that at least one or each of the magnetic implants represented in FIGS. 7-11 and 20-24 can be associated with a retention member as described herein.

Housing

In some implementations, the magnetic implant 12, 14 can include a housing 22 configured to house a magnet therein. An example of housing 22 is shown in FIGS. 1-6. More particularly in FIGS. 4 and 5, the housing 22 is shown as including an outward portion 26 and an inward portion 28. In the context of the present description, the terms "outward" and "inward" when referring to the housing 22 are used in accordance with a radial reference system, in which the wall of the hollow organ is considered to be outwardly positioned relative to the lumen of the hollow organ. When the housing 22 is present, the outward portion 26 of the housing 22 is the portion that includes the lumen-oriented surface 42 of the magnetic implant, and the inward portion 28 of the housing 22 is the portion that includes the tissue-contacting surface or the compression surface 30. In the implementation shown, the outward portion 26 and the inward portion 28 together fully enclose a single magnet 24 therein. In other implementations, the single magnet can be fully enclosed in a single-piece housing, i.e., a housing 22 that is made of a single unit, the single unit including the tissue-contacting surface 30 and the lumen-oriented surface, 42 in accordance with the description above.

In some implementations, the magnetic implant can include a housing that is configured to receive multiple magnets therein. Providing multiple magnets within a single housing can contribute to enhancing the flexibility of the magnetic implant, such that it can become easier to bend when subjected to a force. Alternatively, the multiple magnets can each be received in a corresponding housing, and the multiple magnets can be connected to each other by a cable, a string, a ribbon, a hitch, or a combination thereof, as described above. In implementations where each magnet is received in a corresponding housing, the various configurations described above in reference to FIGS. 9-11 are similarly applicable, although in this case multiple housings are present.

In the same order of ideas, the description made above regarding the characteristics of the compression surface 30 of the magnetic implant is applicable to the housing 22 when the housing is present or when housings are present.

Description of the Retention Member

Referring back to FIGS. 1 to 6, the system 10 for forming an anastomosis between two adjacent walls of hollow organs of the digestive tract further includes a retention member 16 that extends, or projects, outwardly from a corresponding one of the first and second magnetic implants 12, 14. Reference to an outward extension when describing the retention member 16 is also made in accordance with a radial reference system, with an outward extension meaning an extension or projection away from the compression surface 30 of the magnetic implant, e.g., away from a center of the compression surface 30 of the magnetic implant.

The retention member 16 can be any structure that enables the retention of the pair of magnetic implants 12, 14 in position once magnetically coupled and during the healing time period, to prevent the first and second magnetic implants 12, 14 to prematurely pass through the necrotic area.

In some implementations, the retention member 16 can also be any structure that enables providing additional buttress to the magnetic implant during the healing time period, and the retention member 16 may be configured such that it applies a pressure that may be sufficient to cause necrosis but at a slower rate than the necrosis occurring between the compression surfaces 30 of the magnetic implants 12, 14 once they are magnetically coupled. The magnetic implants 12, 14 and the retention members 16 can then eventually separate from the healed anastomosis and pass into the stool.

In other implementations, the retention member 16 can be configured to apply additional buttress to the anastomosis by engaging the periphery of the anastomosis at a pressure interference amount that does not result in necrosis of the tissue that is in contact with the retention member 16. In such implementations, the retention member "footprint" is larger than the desired anastomosis, and the interference resulting from the presence of the retention member 16 can prevent the magnetic implants 12, 14 from passing though the anastomosis even after the tissue has necrosed between the compression surfaces 30 of the magnetic implants 12, 14 and the tissue has separated from the anastomosis. In such implementations, the retention member 16 can be formed of a bioresorbable material that is configured to resorb at a given timepoint during the healing time period and eventually disintegrates to the point where the interference is no longer sufficient to maintain the pair of magnetic implants 12, 14 in place at the anastomosis site, and the magnetic implants 12, 14 are now small enough to pass through the anastomosis and be eliminated in the stool.

The retention member 16 can thus be configured to provide enough time for the scar edge to form during the healing time period, and also to provide additional buttress or strength to keep the magnetic implants 12, 14 from decoupling or the tissue from perforating or tearing due to loads on the anastomosis site and connected bowel and stomach tissues. Examples of external or internal loads can include the weight of the bowel or stomach moving due to patient movement and/or internal loads from peristalsis, bowel spasm/constriction, and internal gas pressure changes.

In some implementations, the retention member 16 can be configured to provide additional mechanical support to prevent premature separation of the magnetic implants 12, 14, tissue stretching/tearing or leak due to physiologic loads that can result for instance from the weight of the bowel segments and the forces imparted by patient movement, spasm/constriction of the vessels, internal gas pressure changes, etc., on the healing anastomosis site and connected vessels.

In some implementations, the retention member 16 can be configured is so as to not impart enough compression to cause necrosis but to provide an additional surface area to distribute the physiologic loads during healing. As such, the retention member 16 can be configured to be in intimate contact with the outside surface of the vessel wall once the compression surfaces 30 are magnetically coupled and has compressed the tissues.

Figure 16:
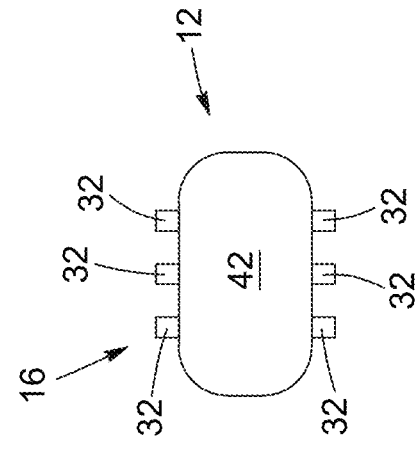
FIG. 16 is a top view of a magnetic implant that includes a series of flanges, with a first flange at 12 o'clock, a second flange at 3 o'clock, a third flange at 6 o'clock, and a fourth flange at 9 o'clock, in accordance with another implementation.
Figure 17:
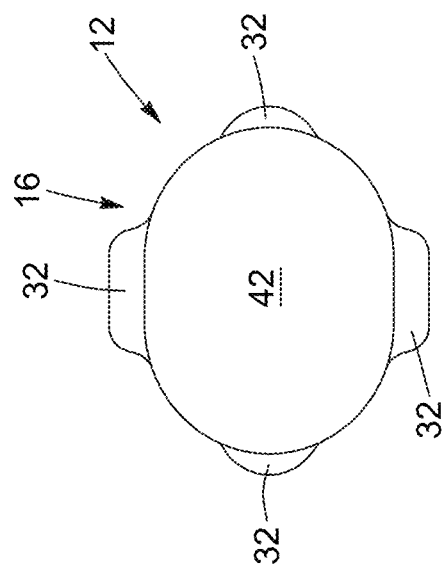
FIG. 17 is a top view of a magnetic implant that includes a series of flanges provided in a spaced-apart relationship around a periphery of the magnetic implant, in accordance with another implementation.

In some implementations and with reference to FIGS. 1-6, and 12-15, the retention member 16 can include a flange 32 that extends continuously around substantially the entire periphery of the corresponding magnetic implant. The flange 32 may extend around the entire periphery or may extend around all but a small portion of the periphery. In other implementations and with reference to FIGS. 16 and 17, the retention member 16 can include a series of flange extensions that are provided in a spaced-apart relationship around the periphery of the corresponding magnetic implant. When a series of flange extensions is provided as the retention member 16, the flange extensions are disposed as discrete flanges located at given locations, i.e., extending radially, around the periphery of the corresponding magnetic implant and in a number such that the retention member 16 can retain the pair of magnetic implants 12, 14 once implanted in the digestive tract of the patient and magnetically coupled. An example of a series of flanges can include a first flange and a second flange diametrically opposed to the first flange. Another example of a series of flanges can include a first flange at 12 o'clock, a second flange at 3 o'clock, a third flange at 6 o'clock, and a fourth flange at 9 o'clock, such as shown in FIG. 16. The location and number of the flanges of a series of flanges can be determined at least in part by the characteristics of the tissue against which the magnetic implant will rest, the desired stability of the magnetic implant once implanted in the digestive tract, the material of which is made the flanges, and the mechanism by which the flanges can eventually defeat, among others. The size of the flanges, when provided as a series of discrete flanges, can also vary according to various factors. In some implementations, the flanges can be thin flanges that are smaller width compared to their length. In such implementations, the flanges can be referred to as discrete arms, or discrete fingers.

Figure 12:
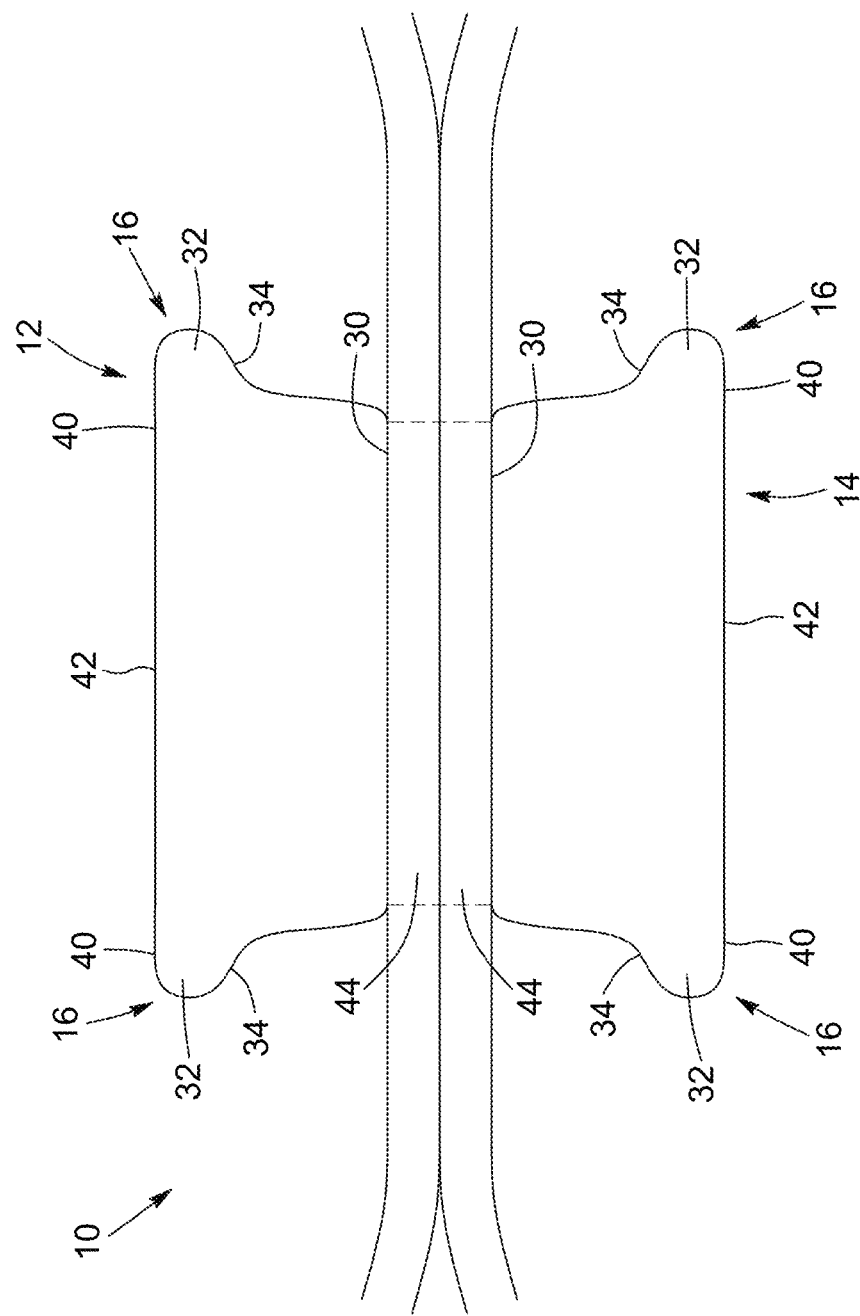
FIG. 12 is a side view of first and second magnetic implants and corresponding retention members, with the first magnetic implant being shown in contact with a vessel wall of a first hollow organ and the second magnetic implant being shown in contact with a vessel wall of a second hollow organ, at the desired site of the anastomosis, in accordance with another implementation.
Figure 13:
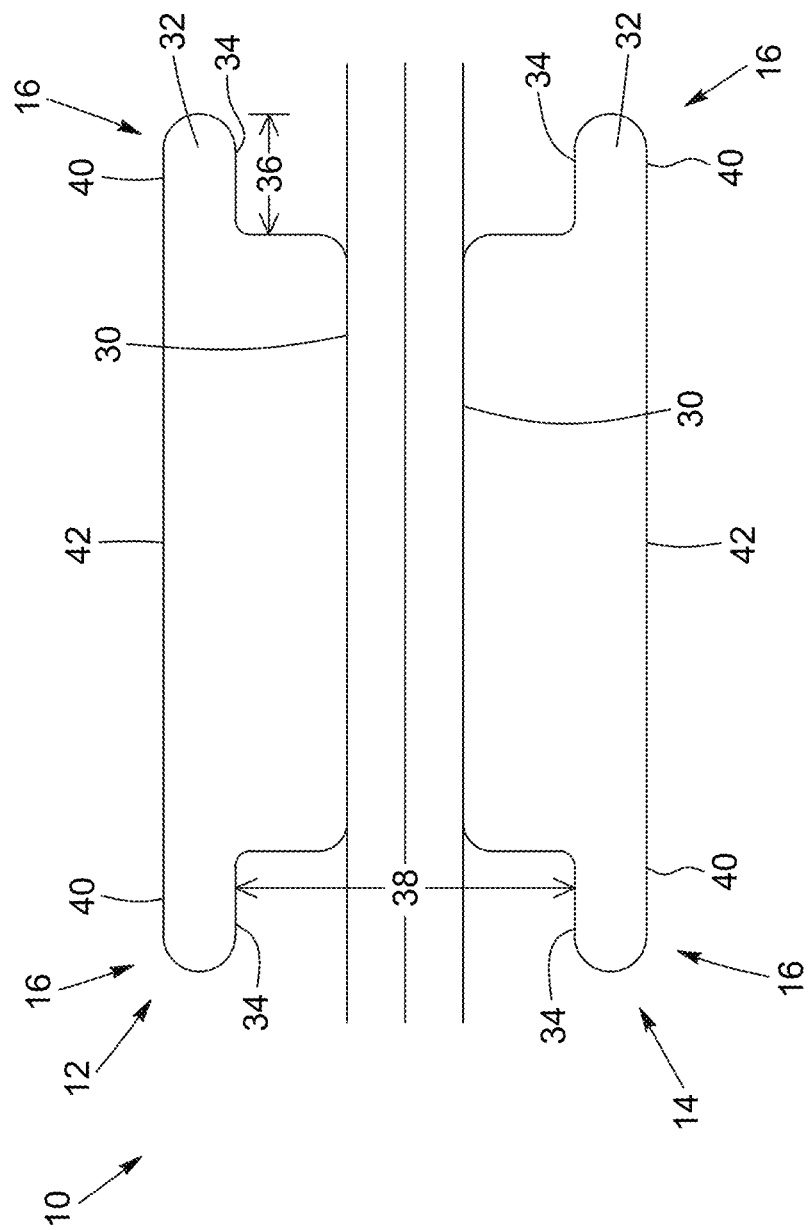
FIG. 13 is a side view of first and second magnetic implants and corresponding retention members, with the first magnetic implant being shown in contact with a vessel wall of a first hollow organ and the second magnetic implant being shown in contact with a vessel wall of a second hollow organ, at the desired site of the anastomosis, in accordance with another implementation.
Figure 14:
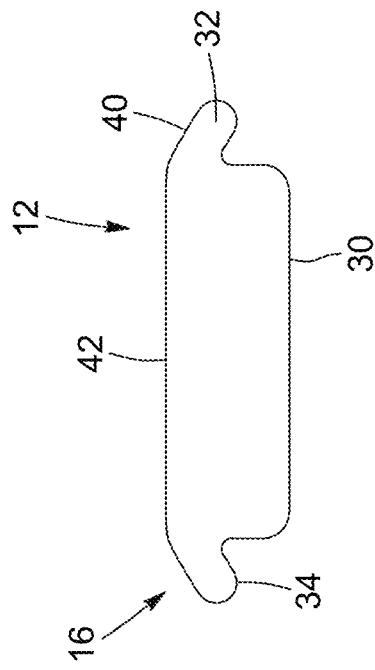
FIG. 14 is a side view of a magnetic implant and of a retention member provided at an angle relative to a compression surface of the magnetic implant, in accordance with another implementation.
Figure 15:
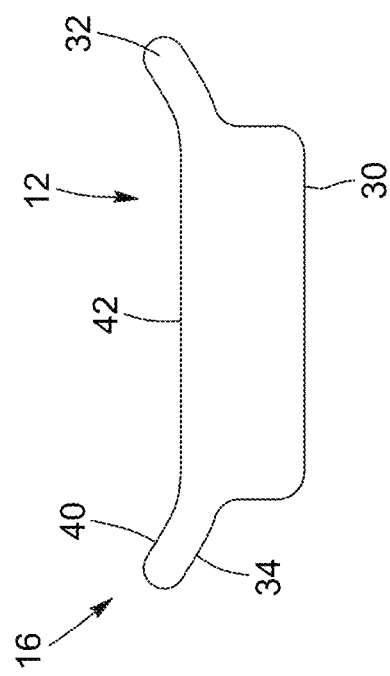
FIG. 15 is a side view of a magnetic implant and of a retention member provided at an angle relative to a compression surface of the magnetic implant, in accordance with another implementation.

With reference to FIGS. 12 and 13, the retention member 16 comprises an outwardly-extending inner surface 34 oriented toward the tissue of the digestive tract. The outwardly-extending inner surface 34 can include a curvature, as shown in FIG. 12, or can be substantially flat, as shown in FIG. 13. In some implementations, the length 36 of the outwardly-extending inner surface 34 is chosen so as to retain the corresponding magnetic implant in position during the healing time period, once the magnetic implants 12, 14 are magnetically coupled to each other. The length 36 of the outwardly-extending inner surface can be for instance between about 0.5 mm and about 10 mm.

In addition, the retention members 16 of a pair of magnetic implants 12, 14 can be configured to maintain a gap 38 between the outwardly-extending inner surface 34 of a first magnetic implant 12 and the outwardly-extending inner surface 34 of a second magnetic implant 14 once implanted in the digestive tract. In some implementations, the gap 38 can be such that a space remains between the outwardly-extending inner surface 34 and the outer surface of the vessel, such as shown in FIG. 13. In other implementations, the gap 38 can be such that the outwardly-extending inner surface 34 contacts or gently presses the outer surface of the vessel, such as shown in FIG. 19.

In some implementations, the gap 38 can be for instance at least 0.2 mm or at least 10.0 mm. In some implementations, the gap 38 can be between 0.2 mm and 10 mm.

Figure 30A:
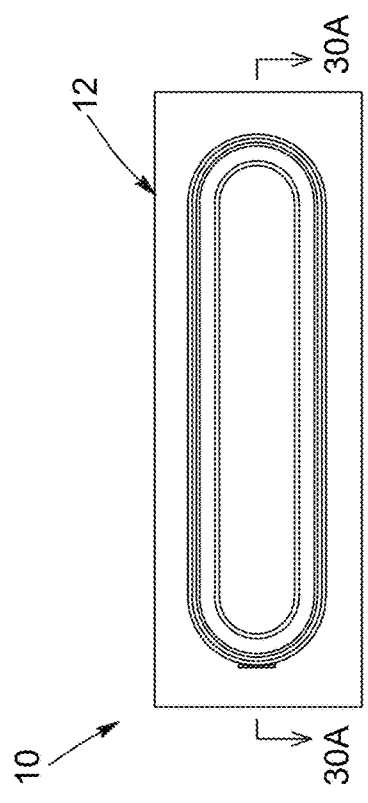
FIG. 30A is a top view of first and second magnetic implants and corresponding retention members, the first magnetic implant being shown in contact with a vessel wall of a first hollow organ, in accordance with an implementation.
Figure 30B:
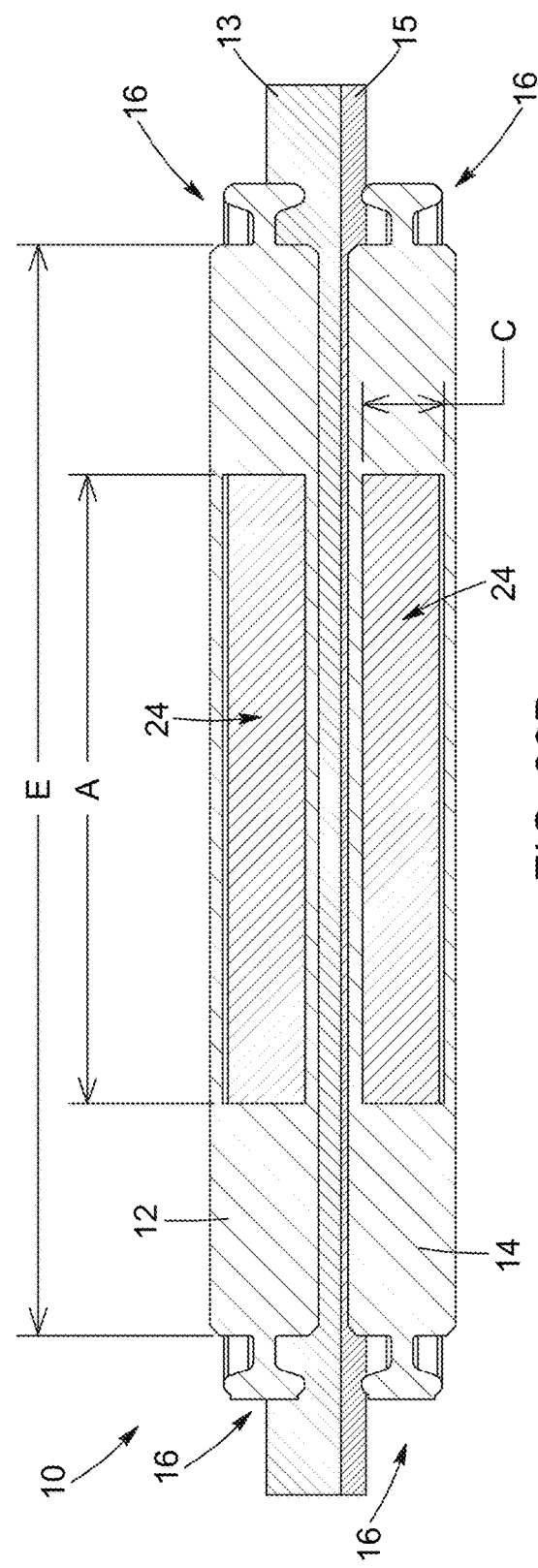
FIG. 30B is a side cross-sectional view of the first and second magnetic implant and corresponding retention members of FIG. 30A, the second magnetic implant being shown in contact with a vessel wall of a second hollow organ.
Figure 30C:
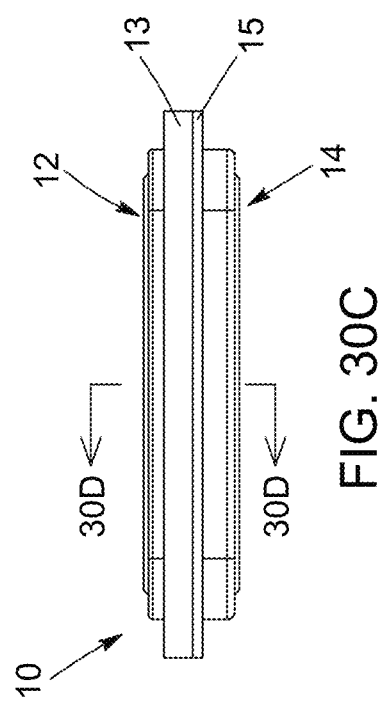
FIG. 30C is a side view of the first and second magnetic implant and corresponding retention members of FIG. 30A.
Figure 30D:
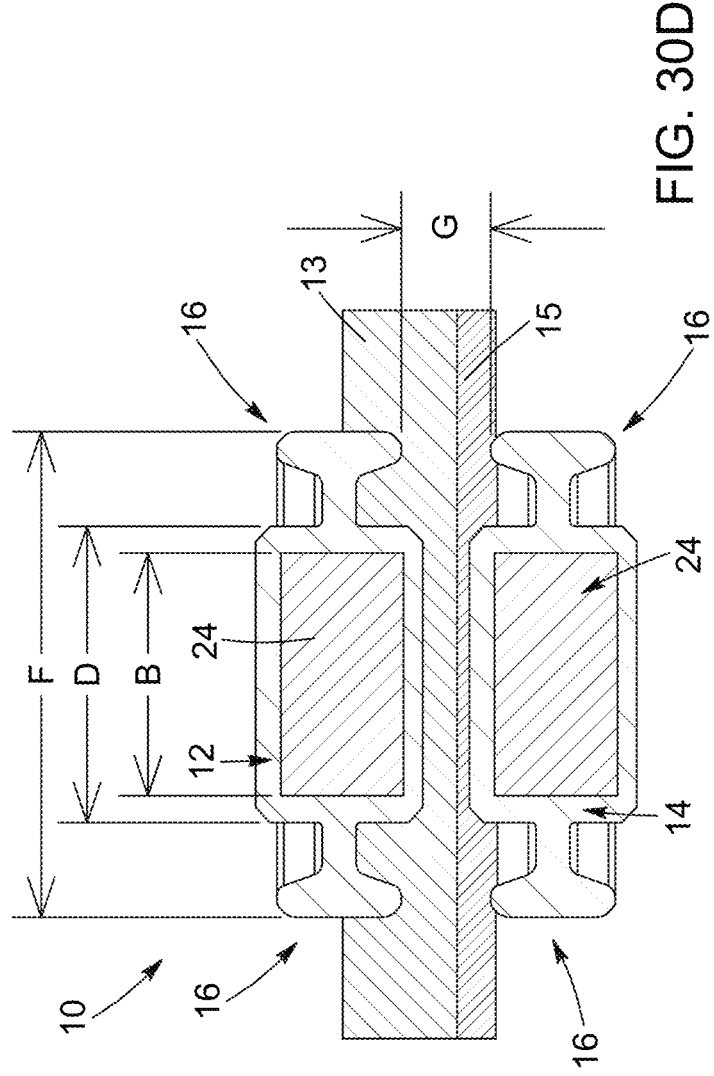
FIG. 30D is a front cross-sectional view of the first and second magnetic implant and corresponding retention members of FIG. 30A.

FIGS. 30A-30D illustrate another example of a pair of magnetic implants 12, 14 being magnetically coupled to each other through the vessel wall of the stomach, shown in dark pink, and the vessel wall of the jejunum, shown in pale pink. In FIG. 30D, the gap 38 is shown as "G", and the retention member 16 is shown as having a T-shaped configuration when viewed as a cross-section. In FIGS. 30A-30D, the retention member 16 is provided alongside the periphery of the housing 22 of each of the magnetic implants 12, 14.

Examples of approximate dimensions, in millimeters, that the magnetic implants can have in certain scenarios are provided in Table 1 below, with reference letters A to G being as illustrated in FIGS. 30A-30D.

TABLE 1

|  | A | B | C | D | E | F | G |
|---|---|---|---|---|---|---|---|
| Example #1 | 25.4 | 6.35 | 3.175 | 7.747 | 44.196 | 7.75 | 2.3 |
| Example #2 | 25.4 | 6.35 | 3.175 | 7.747 | 44.196 | 12.7 | 2.3 |
| Example #3 | 25.4 | 6.35 | 3.175 | 7.747 | 44.196 | 16.5 | 2.3 |

In some implementations, the retention member 16 can be rigid and retain its configuration once the magnetic implants 12, 14 are magnetically coupled to each other in the digestive tract, for instance when the outwardly-extending inner surface 34 of the retention member 16 is configured not to contact the outer surface of the vessel.

In other implementations, in order to ensure that the pressure exerted on the tissue located underneath the outwardly-extending inner surface 34 still permits blood to circulate in that area, the retention member 16 can be flexible and/or connected to the magnetic implant in a flexible manner such that the retention member 16 can yield when the two magnetic implants 12, 14 magnetically couple. This feature can enable the combination of the magnetic implant and retention member 16 to adapt to different tissue thickness depending on the hollow organ into which it is implanted. In implementations where the outwardly-extending inner surface 34 of the retention member 16 contacts the outer surface of the vessel, the retention member 16 can also be rigid, as long as the pressure exerted by the outwardly-extending inner surface 34 on the area of the tissue does not result in necrosis of the tissue in that specific area. In some implementations and with reference to FIG. 18, the retention member 16 can include a thinner area 31 that can contribute to enhance the flexibility thereof.

The retention member 16 also includes an outwardly-extending outer surface 40 that can be continuous with a top surface 42, or lumen-oriented surface, of a corresponding magnetic implant, as shown in FIGS. 1-6, 12 and 13. In other implementations, the transition from the outwardly-extending outer surface 40 to the top surface 42 can include a curvature or a step change, for example.

Figure 27:
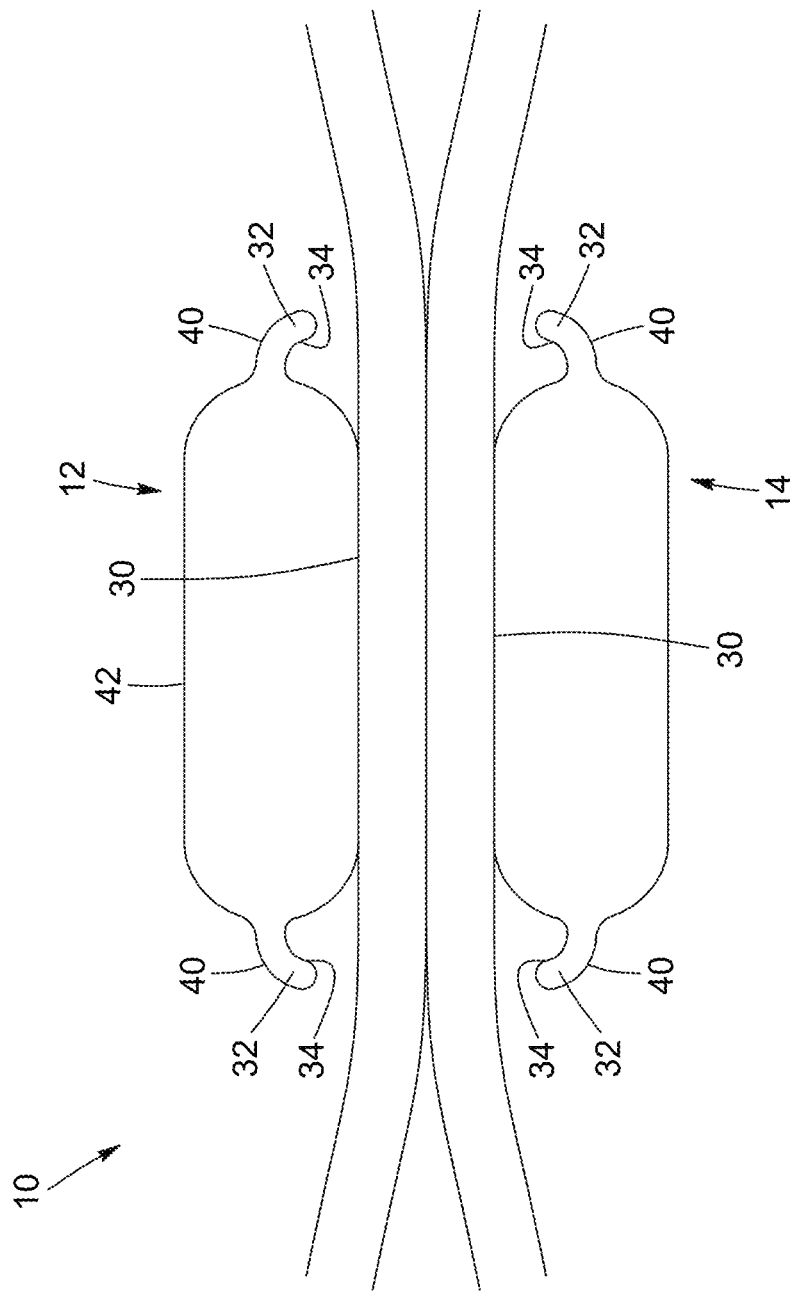
FIG. 27 is a side view of first and second magnetic implants and corresponding retention members, with the first magnetic implant being shown in contact with a vessel wall of a first hollow organ and the second magnetic implant being shown in contact with a vessel wall of a second hollow organ, at the desired site of the anastomosis, in accordance with another implementation.

The retention member 16 can be provided substantially parallelly relative to the compression surface 30 of the magnetic implant, as shown in FIGS. 1-6, 12 and 13. Alternatively, with reference to FIGS. 14 and 15, the retention member 16 can be provided at an angle relative to the compression surface 30. The retention member 16, or flange 32, can be provided at various locations along the height, or thickness, of the magnetic implant. For instance, in the embodiment shown in FIG. 27, the transition from the outwardly-extending outer surface 40 to the top surface 42 includes a step change, such that the retention member 16 is provided in a middle region in terms of the height of the magnetic implant, and the retention member 16 includes a downwardly-oriented curvature, i.e., a curvature that is oriented toward the tissue once the magnetic implant is implanted at the site of the desired anastomosis. In some implementations, a retention member comprising this type of curvature can contribute to avoid compressing the tissue beyond a certain degree of force. In addition, in some implementations and as illustrated in FIG. 27, the retention member 32 of the first magnetic implant 12 can terminate above, or higher, the tissue-contacting surface, or compression surface 30, of the corresponding first magnetic implant 12. The terms "above" or "higher" are used in reference to the outer surface of the organ wall against which the compression surface 30 of the magnetic implant rests. Thus, in FIG. 27, the outwardly-extending inner surface 34 of the first magnetic implant 12 is oriented toward the tissue of the digestive tract and is located above, or higher, than the outer surface of the tissue of the first organ, while the outwardly-extending inner surface 34 of the second magnetic implant 14 can be said to be oriented toward the tissue of the digestive tract and is located below, or lower, than the outer surface of the wall of the first organ.

In some implementations, the retention member 16 can be sized and configured so as to prevent passage of the pair of magnetic implants 12, 14 through the necrosis area during the healing time period due to increased edema and spasm/constriction, but once healed, i.e., absence of edema and spasm/constriction, etc., the size and configuration of the retention member 16, in combination with physiologic loading stretching, compliance, and flexibility of the vessel walls eventually enables the magnetically coupled pair of magnetic implants 12, 14 to pass and exit the body of the patient. In some implementations, this scenario can be achieved without the use of bioresorbable materials being present in the retention member 16.

In some implementations, the retention member 16 can be configured such that once the magnetic implants are magnetically coupled, the retention members 16 compress the tissues to the point of necrosis or at least apply a gradient of pressure from an inwardmost portion of the retention member 16 extending to an outermost portion of the retention member 16, albeit to a lesser amount of pressure compared to the pressure exerted by the compression surfaces 30 of the magnetic implants, such that a longer period of time may be required for completing the healing compared to the necrosis region defined between the compression surfaces 30.

When the magnetic implant includes a housing 22, the retention member 16 can be provided as an integral structure with the housing 22. This scenario can be envisioned for instance when the housing 22 and the retention member 30 are made of the same material, but can also be implemented when the housing 22 and the retention member 30 are made of the different materials. In other implementations, the retention member 30 can be provided as a discrete structure from the housing 22, and can be attachable, couplable or otherwise engageable with the housing 22.

In some implementations, the retention member 16 is configured to be defeatable once the healing time period is completed. In the context of the present description, the term "defeatable" refers to the capacity of the retention member 16 to modify its configuration or structure once the healing time period is completed, or at a given timepoint during or after the healing time period. The retention member 16 can be defeatable according to various mechanisms of which examples are provided in the following paragraphs.

The retention member 26 can be defeatable for instance mechanically or chemically via dissolution or degradation mechanisms.

When the retention member 16 is defeatable mechanically, it is meant that the retention member 16 has a structure that can be manipulated (e.g., by a person), for instance using an endoscope or externally, to directly or indirectly contact the retention member 16 to move the retention member 16 to a position or configuration that allows passage of the magnetic implants through the anastomosis.

For example, the retention member 16 can include one or more portions that promote the breaking apart of the retention member 16 from the remainder of the magnetic implant to facilitate the passing of the coupled magnetic implants through the necrotic area, which is illustrated as necrotic area 44 in FIG. 12. The breaking apart of the retention member 16 can be facilitated for instance due to the presence of a different material, or due to a given configuration of the retention member 16.

Alternatively, the retention member 16 can include one or more weakened portions, such as thinner portions 31 shown in FIG. 18, or otherwise displaceable portions, that promote folding or displacement of the retention member 16 in a given direction such that the coupled magnetic implants can pass through the necrotic area.

Figure 31:
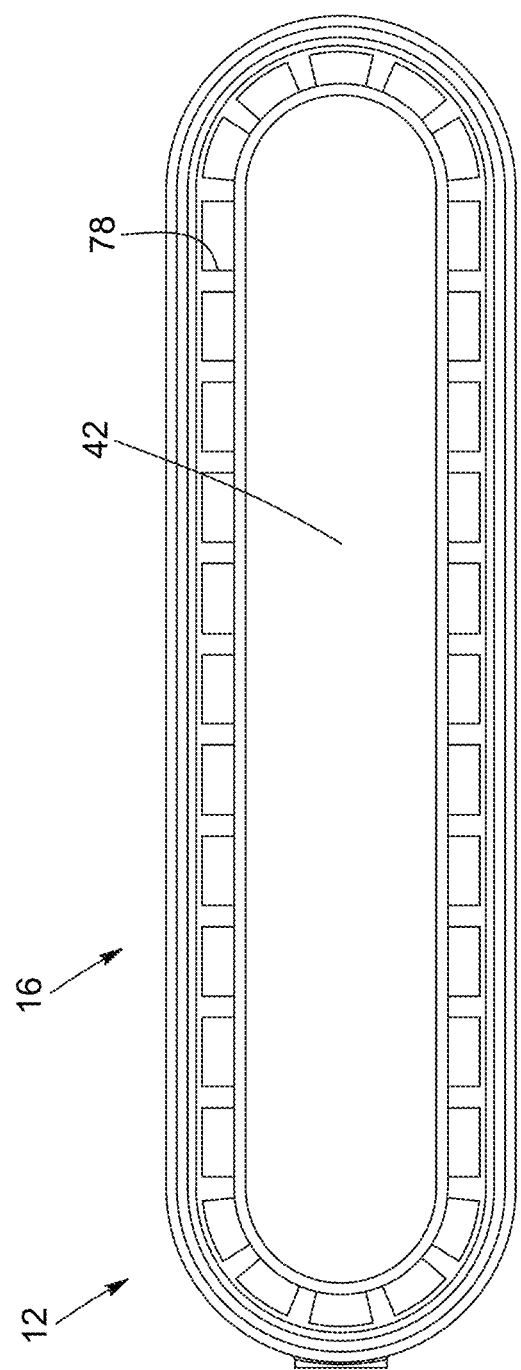
FIG. 31 is a top view of a magnetic implant and of a retention member, the retention member including multiple connection tabs provided in a spaced-apart relationship around an outer periphery of the magnetic implant, in accordance with an implementation.

In some implementations, the retention member 16 can be connected to the housing 22 via multiple connection tabs 78, the multiple connection tabs 78 contributing to increase the surface area thereof which in turn can facilitate dissolution and breaking off of the connection tabs 78. FIG. 31 illustrates a top view of an example of a retention member 16 that includes multiple connection tabs 78 provided in a spaced-apart relationship around an outer periphery of a magnetic implant.

In some implementations, the retention member 16 can include a defeatable portion that is breakable into smaller pieces, which can later on be passed naturally, so as to reduce the size of the retention member 16 so that it can also be passed naturally. The breaking apart or the folding or displacement of the retention member 16 can be achieved by the dissolution, degradation, or fragmentation of the retention member 16 or a portion thereof. In order to do so, the retention member 16 can be made of a material, or can be made of one or more portions made of a material that, when subjected to a particular set of conditions, changes configuration or make-up. In the case of a retention member 16 that is defeatable, the change in configuration is one that facilitate the passing of the coupled magnetic implants through the necrotic area. The set of conditions can include a duration, which can correspond to the healing time period, the pH surrounding the retention member 16, and the temperature surrounding the retention member 16. For instance, it can be determined that a material known to dissolve or disintegrate after about two weeks, at a strong acidic pH and at temperatures of about 37° C. would be suitable to be used for the retention member 16 on a magnetic implant intended to be implanted in the stomach.

In some implementations, the retention member 16 can include a portion that is foldable against the magnetic implant for delivery within the digestive tract, the foldable portion being configured to unfurl once the magnetic implant is implanted within the digestive tract.

In some implementations, the retention member 16 can be configured to adopt a retracted configuration for delivery within the digestive tract, and an expanded configuration once the magnetic implant is implanted in the digestive tract.

The retention member 16 can include a biasing mechanism to enable the transition from the retracted configuration to the expanded configuration. The retention member 16 can thus adopt a first configuration, e.g., a folded or retracted configuration, that facilitates its for delivery to the site of the desired anastomosis, and a second configuration, e.g., unfolded or expanded, that enables the retention member 16 to fulfill its intended purpose of retaining the coupled magnetic implants in position once delivered and implanted at the site of the desired anastomosis. The first configuration can be one where the retention member 16 has smaller dimensions such that it can be more easily navigated within the hollow organ of the digestive tract. In contrast, the second configuration can be one where the retention member is spread out and is capable of retaining the coupled magnetic implants in position once implanted at the site of the desired anastomosis and during the healing time period.

The retention member 16 can be configured such that the coupled magnetic implants are passed via manipulation of an external magnet or by an endoscopic device. In other implementations, the retention member 16 can be configured such that the coupled magnetic implants are passed naturally at the end of the healing time period, i.e., without external manipulation.

In some implementations, the shape, size, and/or configuration of the first magnetic implant can be similar to the configuration of the second magnetic implant. In other implementations, the shape, size, and/or configuration of the first magnetic implant can be different from the configuration of the second magnetic implant. The choice of whether to use a pair of magnetic implants that include similar or different magnetic implants can depend for instance of the hollow organ into which the respective magnetic implants will be implanted. Whether or not the magnetic implants are similar, the retention member of the respective magnetic implant can also be similar or different, in terms of size, shape, and/or configuration. Once again, the respective hollow organs into which the magnetic implants will eventually be implanted can be a factor in determining whether the corresponding retention member could be similar or different.

Materials

Details regarding different materials that the retention member 16 and the housing 22, if present, can be made of will now be provided.

In some implementations, the retention member 16 can be made of or include a bioerodible material, biodegradable material, and/or bioresorbable material. A bioerodible material, such as a bioerodible hydrogel, refers to a material, such as a polymer, that exhibits a controlled degradation in a given environment such as under physiological conditions, for instance by undergoing surface erosion. A biodegradable material refers to a material that is susceptible to breakdown, decomposition or degradation under the action of biological processes, such as by enzymatic action. A bioresorbable material refers to a material that can be resorbed or dissolved naturally under physiological conditions. As mentioned above when describing the scenario where the retention member 16 can be defeatable, a retention member 16 that is made of or that includes one or more portions that are made of a bioerodible material, a biodegradable material, or a bioresorbable material provides the retention member 16 with an initial shape and initial dimensions that enable the retention member 16 to retain the coupled magnetic implants in position during the healing time period while over time, the dimensions of the retention member 16 are eventually reduced sufficiently to pass through the necrotic area and be evacuated either naturally or with the support of an external means, for instance via resorption of the retention member 16 itself, or following breaking into passable sized objects.

For instance, the retention member 16 can be made of an aliphatic polyester or a combination of aliphatic polyesters, or can include one or more portions made of an aliphatic polyester or a combination of aliphatic polyesters. The aliphatic polyester can be a synthetic aliphatic polyester. Examples of aliphatic polyester include polylactic acid, polyglycolic acid, polylactic-co-glycolic acid, polycaprolactone, and polydioxanone.

The retention member 16 can be made of at least two materials, each of the materials having a different dissolution rate or a different degradation rate once implanted in a given environment, and in this case, in the respective hollow organ into which is implanted the magnetic implant. The difference in dissolution rate or degradation rate between the at least two materials can result in certain pre-determined portions of the retention member 16 to weaken, which in turn can promote the defeatability of the retention member 16. The pre-determined portions of the retention member 16 can be for instance notches or thin spots provided at strategic locations. In some implementations, the dissolution and/or degradation occurring at these strategic locations can be dependent on the pH of the environment where it is implanted. For instance, one or more pre-determined portions of the retention member 16 can be subjected to an accelerated dissolution and/or degradation in a strongly acidic environment compared to a weakly acidic environment. Alternatively, one or more pre-determined portions of the retention member 16 can be subjected to an accelerated dissolution and/or degradation in a basic environment compared to an acidic environment, for instance when the magnetic implant is intended to be in contact with pancreatic juice, bile and/or pancreatic enzymes. Other considerations that can influence the degradation of the one or more pre-determined portions of the retention member 16 can include the presence of bacteria with or without lytic enzymes, and possible drugs interactions such as with H2-receptor blockers or proton pump inhibitors.

In some implementations, the retention member 16 of both the first magnetic implant 12 and the second magnetic implant 14 can be made of the same material. This scenario can be implemented for instance when the physiological environment of the corresponding two hollow organs of the digestive tract is similar. A similar physiological environment can refer for example to the approximately neutral pH within two segments of the small intestine.

In other implementations, given the property of bioerodible materials, biodegradable materials, or bioresorbable materials to erode, dissolve or degrade at a given rate depending on the environment, a first material can be chosen for the retention member 16 of the first magnetic implant 12 for implantation in a given hollow organ, and a second material, different from the first material, can be chosen for the retention member 16 of the second magnetic implant 14 for implantation in a different given hollow organ. The retention member 16 of the first magnetic implant 12 and the retention member 16 of the second magnetic implant 14 can then dissolve or degrade based on the differences in the physiological environment in the respective hollow organs over the healing time period. For example, when the first magnetic implant 12 is intended to be implanted in the stomach, where the pH is strongly acidic, and the second magnetic implant 14 is intended to be implanted in the jejunum, where the pH is weakly acidic, the material of the retention member 16 of the first magnetic implant 12 can be different from the material of the retention member 16 of the second magnetic implant so as to obtain a similar dissolution rate or degradation rate between the two retention members 16. In other words, the design of each retention member can be based on the properties of the hollow organ and corresponding tissue wall (including the tissue thickness, tissue surface characteristics, internal pH and conditions of the hollow organ, and/or other physiological properties) such that the two retention members are defeated after approximately the same time interval.

In other implementations, the retention member 16 can comprise a material that is generally not susceptible to dissolution or degradation, and that would be considered a durable material once implanted in the hollow organ. Examples of such materials can be polymers such as silicones, e.g., polydimethylsiloxane; or a fluoropolymer, e.g., polytetrafluoroethylene. Other examples can include a titanium alloy, cobalt chromium, or an austenitic stainless steel. Other examples can also include any other suitable biocompatible material that retains its integrity for a duration longer than the healing time period.

In some implementations, the magnetic implant on the distal side of the anastomosis, i.e., further away from the mouth of the patient, may be associated with a larger retention member than the retention member associated with the magnetic implant located on the proximal side since the distal side of the magnetic implant does not have to pass through the anastomosis, i.e., for natural elimination, as it is already distal to the anastomosis. In some implementations, the retention member on the distal side of the anastomosis can be non-resorbable.

The retention member 16 can also be made of a self-expandable material or of a shape-memory material. An example of a shape-memory alloy is nitinol. Nitinol is a nickel-titanium shape-memory alloy, and has a shape that is temperature dependent. Other examples of shape-memory materials can include shape-memory polymers. The self-expandable material can enable the retention member 16 to adopt a constrained configuration for delivery to the site of the desired anastomosis, and once the constraint is removed, i.e., once the magnetic implant is delivered to the site of the desired anastomosis, the retention member 16 can adopt a deployed configuration that enables the retention member 16 to retain the magnetic implant in position during the healing time period. In implementations where the retention member 16 is made of a temperature-dependent shape-memory material, the retention member 16 can also adopt a constrained configuration for delivery to the site of the desired anastomosis, and once the magnetic implant is delivered to the site of the desired anastomosis and thus following exposure to physiological temperatures, the retention member 16 can resume its original shape, which can correspond to a deployed configuration that enables the retention member 16 to retain the magnetic implant in position during the healing time period.

Additional Considerations Regarding the Housing and the Retention Member

In implementations where the magnetic implant includes a housing 22, various scenarios are possible with regard to the respective materials of which they can be made. The housing 22 and the retention member 16 can be made of similar or same materials. This scenario can enable the housing 22, or a portion thereof, and the retention member 16 to be manufactured in a same manufacturing process, such that the housing 22 and the retention member 16 are integral with each other, or in different manufacturing processes. Alternatively, the housing 22, or a portion thereof, and the retention member 16 can be made of different materials. In this scenario, the housing 22 and the retention member 16 can be manufactured in a same manufacturing process or in different manufacturing processes. When the housing 22 and the retention member 16 are manufactured in different manufacturing processes, the retention member 16 is configured to be attachable, connectable, couplable, or engageable to/with the housing 22 following the different manufacturing process.

In some implementations, an additive manufacturing method can be used to manufacture the housing 22 and/or the retention member 16. An additive manufacturing method can refer to a method for manufacturing a three-dimensional object by adding layer over layer of given material(s) to obtain a plurality of layers according to a three-dimensional model, the plurality of successive layers being bonded together, for instance by sintering or melting, to form the three-dimensional object. In some implementations, the additive manufacturing method is a 3D printing method. The additive manufacturing method can facilitate the production of objects having complex geometries, compared to conventional subtractive methods.

Additive manufacturing methods encompass a broad spectrum of methods, such as, but not limited to, binder jetting, directed energy deposition, material extrusion such as fused deposition modeling (FDM), material jetting, powder bed fusion, sheet lamination, vat photopolymerization, combinations thereof, or any other method(s) as known in the art.

In some implementations, the housing 22 may be formed of one or multiple pieces. For instance, FIG. 5 shows a magnetic implant 10 that includes a housing having a top and bottom portions with a parting line where they mate together once assembled, also referred to as the outward portion 26 and the outward portion 28. The parting line may be incorporated anywhere along the thickness of the magnetic implant. The clamshell construction allows for easy assembly and encapsulation of the component parts that reside within the housing 22, such as the magnet, the delivery system attachment mechanisms, etc. The housing 22 and its internal components may be bonded together using adhesives or thermally reflowed or overmolded if the housing 22 is formed of a thermoplastic resin. If the housing 22 is made of a metallic material, the parting line of the top and bottom housing may be laser welded to bond the housing together and create a hermetic seal around the magnetic core, or magnet 24.

Housing and/or Retention Member Having Drug-Delivery Properties

In some implementations, the housing, if present, and/or the retention member can be configured to enable release of a given drug therefrom. In order to do so, the housing and/or the retention member can be made of a material that acts as a matrix that includes the given drug, or peptide, with the drug being progressively released as the material undergoes degradation once subjected to certain environmental conditions. In such implementations, the housing and/or the retention member can be said to act as a controlled drug delivery system. Such controlled drug delivery system can advantageously deliver a given drug locally in the region where the anastomosis is forming. The drug that may be chosen to be delivered in the localized region of the anastomosis can be for instance a drug that have pro-thrombosis properties, or any type of wound-healing properties. The housing and/or retention member can thus be designed to offer an opportunity to deliver a drug than can influence the healing process of the anastomosis and formation of the scarred edge, with the housing and/or the retention member thereby each playing an additional role in the formation of the anastomosis. Various materials can be used to provide the controlled drug delivery system, which can also be referred to as a delivery matrix. In some implementations, the delivery matrix forming the housing and/or the retention member can include a bioerodible material such as polylactic acid, polyglycolic acid, and polylactic-co-glycolic acid. In other implementations, the delivery matrix can include a durable material such as polydimethylsiloxane (silicone). Any other type of biocompatible material that enables achieving a sustained drug release therefrom can be considered within the scope of the present description.

Examples of pro-thrombosis drugs, or antifibrinolytic drugs, include tranexamic acid, aprotinin, epsilon-aminocaproic acid, aminomethylbenzoic acid, and aminocaproic acid. Other examples of drug that can be delivered and released locally at the anastomosis region can include insulin, matrikines, and antibiotics.

Examples of peptides having wound-healing properties that can be included within the housing and/or the retention member to be released therefrom are listed in Table 2 and Table 3 below.

TABLE 2

Examples of wound-healing peptides having antimicrobial properties

| Peptide Name | Peptide Sequence |
| --- | --- |
| AG30 | MLSLIFLHRLKSIVIRKRLDRKLRLWHRKNYP (SEQ ID NO: 1) |
| AG30/5C | MLKLIFLHRLKRMRKRLKRKLRLWHRKRYK (SEQ ID NO: 2) |
| AH90 | ATAWDFGPHGLLPIRPIRIRPLCG (SEQ ID NO: 3) |
| CW49 | APFRMGICTTN (SEQ ID NO: 4) |
| Cys-KR12 | CKRIVKRIKKWLR (SEQ ID NO: 5) |
| Esculentin-1a(1-21) | GIFSKLAGKKIKNLLISGLKG (SEQ ID NO: 6) |
| hBD-1 | DHYNCVSSGGQCLYSACPIFTKIQGTCYRGKAKCCK (SEQ ID NO: 7)<br>(Disulfide bridges: 5-34, 12-27, 17-35) |
| hBD-2 | GIGDPVTCLKSGAICHPVFCPRRYKQIGTCGLPGTKCCKKP (SEQ ID NO: 8)<br>(Disulfide bridges: 8-37, 15-30, 20-38) |
| hBD-3 | GIINTLQKYYCRVRGGRCAVLSCLPKEEQIGKCSTRGRKCCRRKK (SEQ ID NO: 9)<br>(Disulfide bridges: 11-40, 18-33, 23-41) |
| hBD-4 | ELDRICGYGTARCRKKCRSQEYRIGRCPNTYACCLRK (SEQ ID NO: 10)<br>(Disulfide bridges: 6-33; 13-27; 17-34) |
| Histatin-1 | DSHEKRHHGYRRKFHEKHHSHREFPFYGDYGSNYLYDN (SEQ ID NO: 11) |
| Histatin-2 | RKFHEKHHSHREFPFYGDYGSNYLYDN (SEQ ID NO: 12) |
| Histatin-3 | DSHAKRHHGYKRKFHEKHHSHRGYRSNYLYDN (SEQ ID NO: 13) |
| IDR-1018 | VRLIVAVRIWRR (SEQ ID NO: 14) |
| LL-37 | LLGDFFRKSKEKIGKEFKRIVQRIKDFLRNLVPRTES (SEQ ID NO: 15) |
| MSI-78 (pexiganan) | GIGKFLKKAKKFGKAFVKILKK (SEQ ID NO: 16) |

TABLE 2-continued

Examples of wound-healing peptides having antimicrobial properties

| Peptide Name | Peptide Sequence |
|---|---|
| Pep19-2.5 | GCKKYRRFRWKFKGKFWFWG (SEQ ID NO: 17) |
| PLL-37 | PLLGDFFRKSKEKIGKEFKRIVQRIKDFLRNLVPRTES (SEQ ID NO: 18) |
| SHAP1 | APKAMKLLKKLLKLQKKGI (SEQ ID NO: 19) |
| SR-0007 | MLKLIFLHRLKRMRKRLKRK (SEQ ID NO: 20) |
| SR-0379 | MLKLIFLHRLKRMRKRLKRK[1] (SEQ ID NO: 21) |
| Temporin A | FLPLIGRVLSGIL (SEQ ID NO: 22) |
| Temporin B | LLPIVGNLLKSLL (SEQ ID NO: 23) |

[1]Lowercase letters indicate D-amino acid residues; Peptide highlighted in bold was entered into clinical trials for its assessment in the treatment of diabetic foot ulcers; S: phosphoserine.

TABLE 3

Examples of wound-healing peptides

| Peptide Name | Peptide Sequence |
|---|---|
| Ac-PGP | N-acetylated-PGP |
| BioGHK | Biotinylated-GHK |
| Col4-1 | MFRKPIPSTVKA (SEQ ID NO: 24) |
| Comb1 | DINECEIGAPAGEETEVTVEGLEPG (SEQ ID NO: 25) |
| E1 | GETGPAGPAGPIGPVGARGPAGPQGPRGDKGETGEQ (SEQ ID NO: 26) |
| Tiger17 | WCKPKPKPRCH (SEQ ID NO: 27) |
| TP-508 | AGYKPDEGKRGDACEGDSGGPFV (SEQ ID NO: 28) |
| TSN1 | NFQGVQNRFVFGTP (SEQ ID NO: 29) |
| TSN2 | MENAELDVPIQSVFTR (SEQ ID NO: 30) |
| TSN3 | NTDNIYPESSC (SEQ ID NO: 31) |
| TSN4 | PYLGYVFK (SEQ ID NO: 32) |
| TSN5 | MQTVAQLFKTVSSLSLST (SEQ ID NO: 33) |
| TSN6 | HSPDIQLQKGLTFEPIQIK (SEQ ID NO: 34) |
| TSN7 | STITQPYKTLNNARSP (SEQ ID NO: 35) |
| TSN8 | RPGPSPEGTGQSYNY (SEQ ID NO: 36) |
| TSN9 | MENAELDPPYLGYVFK (SEQ ID NO: 37) |
| TSN10 | TGQSYNQYSQRPYLGVYVFK (SEQ ID NO: 38) |
| TSN11 | LYGQTPLETL (SEQ ID NO: 39) |
| TSN12 | ELADSPALEIG (SEQ ID NO: 40) |
| TSN13 | LYGQTPLETLELADSPALEIG (SEQ ID NO: 41) |
| TSN14 | VSGNTVEYALPTLE (SEQ ID NO: 42) |
| TSN15 | LDSPTAPTVQSTALTWRP (SEQ ID NO: 43) |
| TSN16 | LDGSAPGPLYTGSALDF (SEQ ID NO: 44) |
| TSN17 | GSEGVRSGRSG (SEQ ID NO: 45) |
| TSN18 | QPQPLPSPGVGGKN (SEQ ID NO: 46) |

TABLE 3-continued

Examples of wound-healing peptides

| Peptide Name | Peptide Sequence |
|---|---|
| Tylotoin | KCVRQNNKRVCK (SEQ ID NO: 47) |
| UN1 | ELLESYIDGR (SEQ ID NO: 48) |
| UN2 | TATSEYQTFFNPR (SEQ ID NO: 49) |
| UN3 | ELLESYIDGRPTATSEYQTFFNPR (SEQ ID NO: 50) |
| WKYMVm | WKYMVM[1] (SEQ ID NO: 51) |

[1]Lowercase letters indicate D-amino acid residues; Peptide highlighted in bold was entered into clinical trials for its assessment in the treatment of diabetic foot ulcers.

Additional examples of suitable peptides that can be part of the controlled drug delivery system include RADA-16, TDM-621, and TDM-623. RADA-16 is a synthetic amphiphilic peptide that can self-assemble into nanofibers and scaffolds in favor of cell growth, hemostasis and tissue engineering. TDM-621 and TDM-623 can act as hemostatic agents and tissue-sealing agents.

In some implementations, the delivery matrix can be configured to include more than one drug, and be designed to release the drugs in a sequential manner to achieve a certain effect at a given time during the healing time period. For example, the delivery matrix can include tranexamic acid, a wound-healing peptide, and an antibiotic. In such a scenario, the delivery matrix can be designed to release tranexamic acid for instance within 24 hours of the implantation of the magnetic implants, and to release the wound-healing peptide after three or four days following the implantation of the magnetic implants. The delivery matrix can further be designed to release the antibiotic at any time point during the healing period. When the delivery matrix is configured to release more than one drug, the delivery matrix can be designed to release selected drug substantially simultaneously. In some implementations, when both the housing and the retention member are made of a material that serves as a delivery matrix, the delivery matrix forming the housing can include a given drug that is the same as the given drug included in the delivery matrix forming the retention member. Alternatively, when both the housing and the retention member are made of a material that serves as a delivery matrix, the delivery matrix forming the housing can include a drug that is different from the drug included in the delivery matrix forming the retention member.

In some implementations, bioerodible materials can also used in the context of interventions for creating an anastomosis with non-magnetic compressive implants, and other components that can be associated with either magnetic compressive implants or non-magnetic compression implants such as sutures, and staples.

Housing and/or Retention Member Comprising One or More Biologically-Active Components In some implementations, the housing and/or the retention member can include a material that is configured to encapsulate specific types of cells that are intended to eventually be released out of the material and thus in proximity of the anastomosis site, i.e., in the region surrounding the anastomosis site. In such implementations, the housing and/or the retention member can include a biologically active component that can contribute to facilitate the healing process, for instance by promoting fibroblast activity, which in turn can shorten the time for forming the edge of scar tissue and contribute to forming an edge of scar tissue having an increased tensile strength. For instance, in some implementations, the housing and/or retention member can include a material configured to encapsulate fibroblasts, stem cells, or other types of cells, such as a bioresorbable material. The determination of which cells to encapsulate can be made according to the desired effect the cells may have once released from the material which, in the case of the formation of an anastomosis, can be related to wound healing. In some implementations, the material can be a semi-permeable membrane that encapsulates the cells, and also allows for diffusion of oxygen and nutrients into the membrane to provide viable conditions for the cells.

Delivery of the Pair of Magnets

Each one of the first and second magnetic implants 12, 14 can include a connecting member connectable to a corresponding connector extending from a corresponding endoscope to be releasably engageable with the connector. The corresponding connector can be for instance a delivery catheter 20. With reference to FIG. 5, when the connector is a delivery catheter, the connecting member can include a delivery catheter attachment assembly 46 connectable to the delivery catheter 20.

FIGS. 20-24 illustrate additional implementations of a connecting member connectable to a delivery catheter 20. Although not explicitly shown in these Figures, it is to be understood that at least one of the magnetic implants represented in FIGS. 20-24 is associated with a retention member as described herein.

Figure 20:
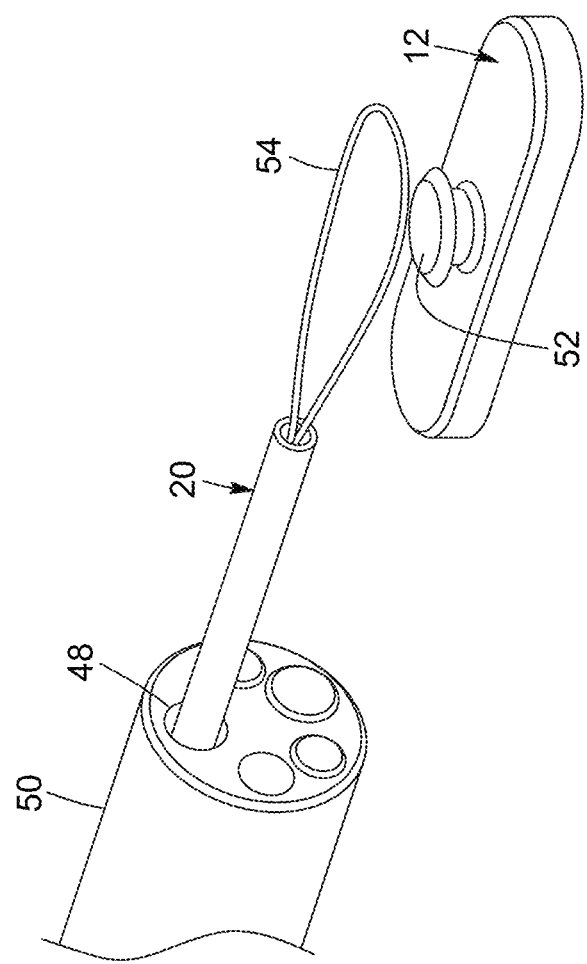
FIG. 20 is a perspective view of a portion of an endoscope, of a delivery catheter loaded into a working channel of the endoscope and that includes a snare, and of a magnetic implant, the magnetic implant including a pommel snare to enable the magnetic implant to be releasably attachable to a distal end of the delivery catheter using the snare, in accordance with an implementation.
Figure 21:
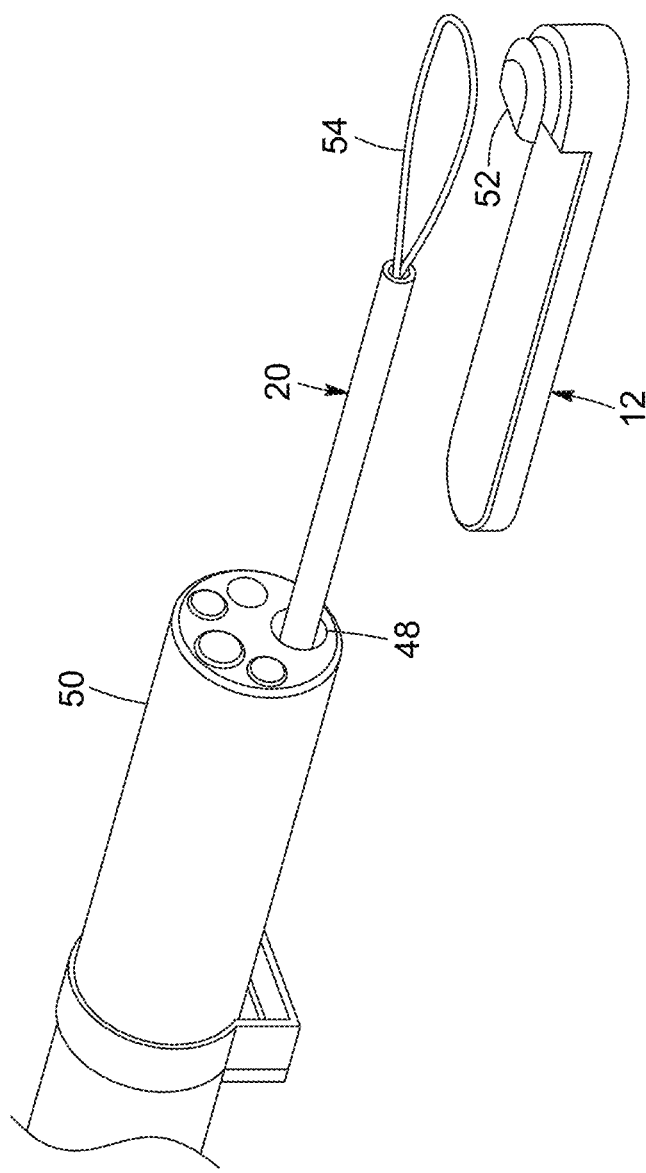
FIG. 21 is a perspective view of a portion of an endoscope, of a delivery catheter loaded into a working channel of the endoscope and that includes a snare, and of a magnetic implant, the magnetic implant including a pommel snare to enable the magnetic implant to be releasably attachable to a distal end of the delivery catheter using the snare, in accordance with another implementation.

In some implementations, the connecting member can include a pommel snare 52, also referred to as a knob feature, as shown in FIGS. 1-6, 20 and 21. In such implementations, the delivery catheter 20 can be loaded into the working channel 48 of an endoscope 50, and the magnetic implant 12 can be releasably attached to the distal end of the delivery catheter 20 using a snare 54 that is wrapped around the pommel snare 52, or knob feature, of the magnetic implant 12. The magnetic implant 12 can be docked onto the delivery catheter 50 by applying tension to the snare wire 54 relative to the delivery catheter 20 and by locking the snare wire 54 relative to the delivery catheter 20 in a handle set that would be positioned at the proximal end of the delivery catheter 20. As can be seen in FIGS. 20 and 21, the pommel snare 52 can be located in a middle portion of the magnetic implant 12, or at a distal end thereof, respectively.

Figure 22:
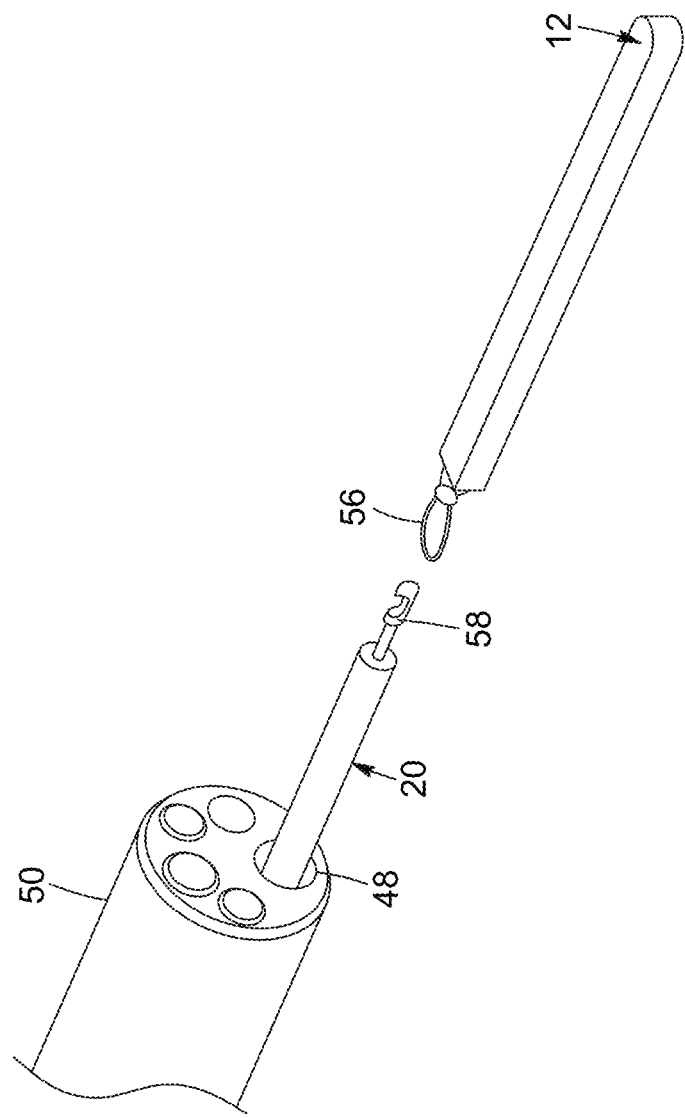
FIG. 22 is a perspective view of a portion of an endoscope, of a delivery catheter loaded into a working channel of the endoscope and that includes a grabber having a U-shaped jaw, and of a magnetic implant that includes a loop to enable the magnetic implant to be releasably attachable to a distal end of the delivery catheter using the grabber, in accordance with an implementation.

With reference to FIG. 22, the connecting member can include a loop 56, and the connector can be a grabber 58 that includes a U-shaped jaw. The grabber 58 can be advanced distally relative to the delivery catheter 20 so that the loop 56 can be able to leave the U-shaped jaw of the grabber 58 once the magnetic implant 12 is delivered to the site of the desired anastomosis.

Figure 23:
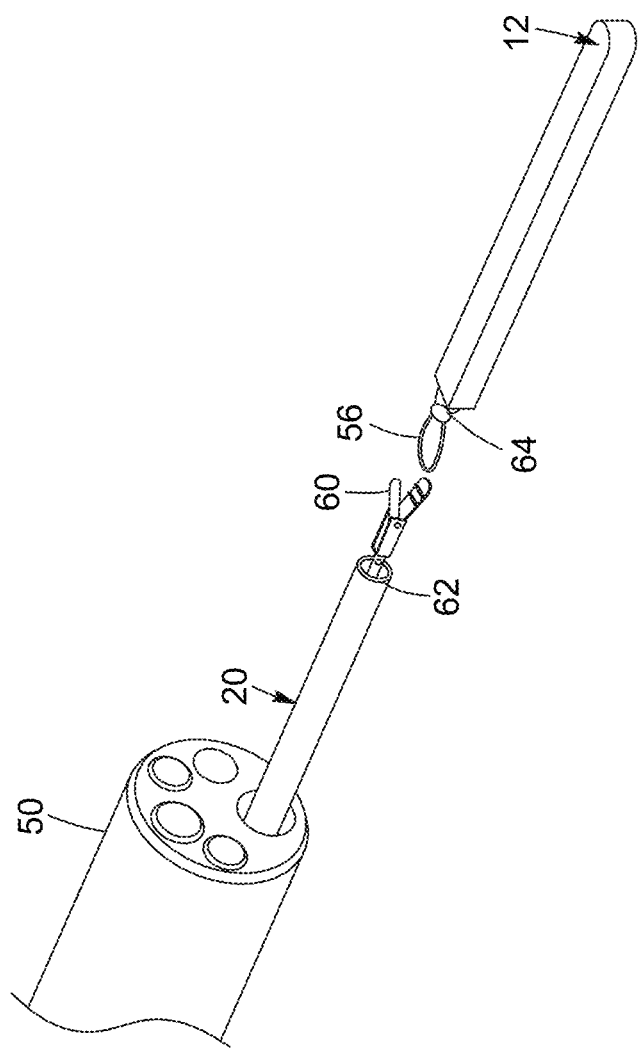
FIG. 23 is a perspective view of a portion of an endoscope, of a delivery catheter loaded into a working channel of the endoscope and that includes a jaw grabber, and of a magnetic implant that includes a loop to enable the magnetic implant to be releasably attachable to a distal end of the delivery catheter using the jaw grabber, in accordance with an implementation.

With reference to FIG. 23, the connecting member can be a loop 56, and the connector can be a mechanically actuated jaw grabber 60. The mechanically actuated jaw grabber 60 can be used to grab the loop 56 instead of the grabber 58 shown in FIG. 22. The mechanically actuated jaw grabber 60 includes a slot cut through it to accept the loop 56, and can pull the loop 56 into the delivery catheter 20 while teeth 62 slide into slot 64 provided on the magnetic implant 12.

Figure 24:
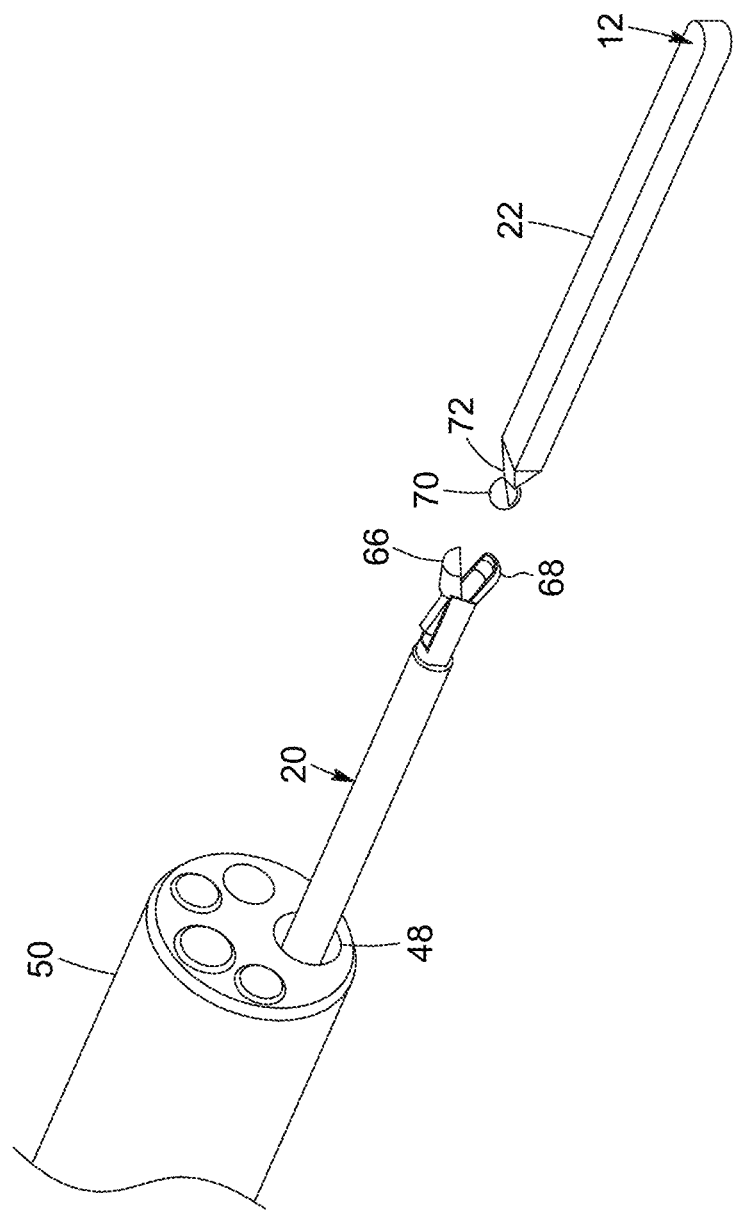
FIG. 24 is a perspective view of a portion of an endoscope, of a delivery catheter loaded into a working channel of the endoscope and that includes a mechanically actuated jaw, and of a magnetic implant that includes a ball to enable the magnetic implant to be releasably attachable to a distal end of the delivery catheter using the mechanically actuated jaw, in accordance with an implementation.

With reference to FIG. 24, the connecting member can be a ball 70, and the connector can be a mechanically actuated jaw 66 that includes a slot feature 68 configured to receive the ball 70 therein. In this implementation, the ball 70 can be part of the housing 22, which can further include a mating bar 72.

The implementations shown in FIGS. 1-6 and 20-24 are provided as examples of various configurations that the connecting member and the connector can take. Accordingly, it is to be understood that the drawings and descriptions herein are proffered by way of example only, and that other types of connector and connecting member can also be suitable to enable the connection of the magnetic implant with a delivery device, such as an endoscope, so that the magnetic implant can be delivered to the site of the desired anastomosis.

Method for Forming an Anastomosis in the Digestive Tract

A method for forming an anastomosis between two adjacent walls of a digestive tract of a patient will now be described in further detail. The method can include navigating a first magnetic implant into the digestive tract of a patient to a first location, on one side of a desired anastomose site, within the lumen of a first hollow organ, and navigating a second magnetic implant into the digestive tract of the patient to a second location on another side of the desired anastomose site, within the lumen of a second hollow organ.

Various techniques can be used to navigate, or deliver, the first and second magnetic implants to the desired site of the anastomosis. It is to be noted that a chosen technique for navigating or deliver the first magnetic implant can be the same or different compared to the chosen technique for navigating or deliver the second magnetic implant. In some implementation, the navigation of the magnetic implant can be performed via a natural cavity of the patient, i.e., the mouth or the anus, using for example an endoscopic device.

In some implementations, navigating the first and second magnetic implants can include releasably engaging the first and second magnetic implants with a corresponding delivery catheter insertable in a working channel of a corresponding endoscope via a connecting member.

In some implementations, at least one of the first and second magnetic implants can be navigated to the site of the desired anastomosis using a laparoscopic procedure. Details regarding various types of suitable laparoscopic procedures and laparoscopic instruments and devices can be found described in U.S. Patent Application No. 2020/0138438A1, which is incorporated herein by reference in its entirety.

Once the magnetic implants are delivered within their respective hollow organ and on their respective side the of the desired anastomosis, the first and second magnetic implants can be brought in close proximity to enable magnetic coupling of the first and second magnetic implants through the two adjacent vessel walls of the digestive tract, such that the compression surface of each of the first and second magnetic implants contacts the interior wall of their respective hollow organ at the site of the desired anastomosis. The magnetic coupling of the two magnetic implants compresses a portion of the two adjacent walls therebetween, and the portion that is compressed between the respective compression surfaces of the magnetic implants eventually forms a necrotic area as the blood flood supply to this area progressively declines.

As at least one of the first and second magnetic implants is associated with a retention member extending outwardly therefrom, the first and second magnetic implants are retained in position on either side of the two adjacent walls during a healing time period to enable formation of a scarred edge surrounding the necrotic area. Retaining the first and second magnetic implants in position during the healing time period prevents the coupled first and second magnetic implants to pass through the necrotic area prematurely, e.g., before the healing time period is completed.

In some implementations, the retention member can be defeatable once the healing time period is completed, and the method can thus further include mechanically defeating the retention member using an endoscope following the healing time period.

In some implementations, the first and second magnetic implants can be manipulated by using a magnet externally, for instance to facilitate the passing of the coupled magnetic implants via the bowel lumen of the patient once the healing time period is completed. An endoscope can also be used to manipulate the coupled magnetic implants internally, also to facilitate their passing via the bowel lumen of the patient once the healing time period is completed.

Several alternative implementations and examples have been described and illustrated herein. The implementations of the technology described above are intended to be exemplary only. A person of ordinary skill in the art would appreciate the features of the individual implementations, and the possible combinations and variations of the components. A person of ordinary skill in the art would further appreciate that any of the implementations could be provided in any combination with the other implementations disclosed herein. It is understood that the technology may be embodied in other specific forms without departing from the central characteristics thereof. The present implementations and examples, therefore, are to be considered in all respects as illustrative and not restrictive, and the technology is not to be limited to the details given herein. Accordingly, while the specific implementations have been illustrated and described, numerous modifications come to mind.

The invention claimed is:

1. A system for forming an anastomosis between two adjacent walls of a digestive tract, the system comprising:

first and second elongated magnetic implants each comprising an outer side wall and a compression surface extending inwardly from a compression perimeter defined by the outer side wall, the first and second elongated magnetic implants being configured for placement within a corresponding hollow organ of the digestive tract and to magnetically couple to each other through the two adjacent walls of the digestive tract to compress a portion of the two adjacent walls therebetween and form a necrotic area that becomes surrounded by a scarred edge following a healing time period; and a retention member extending outwardly from the outer side wall of at least one of the first and second elongated magnetic implants to define a retention member perimeter that is larger than the compression perimeter, the retention member comprising an outwardly-extending inner surface that is spaced back from the compression surface of the at least one of the first and second elongated magnetic implants, the entirety of the retention member being configured to remain within the corresponding hollow organ and retain the first and second elongated magnetic implants in position and prevent passage thereof through the necrotic area during the healing time period.

2. The system of claim 1, wherein the at least one of the first and second elongated magnetic implants comprises a housing configured to house a magnet therein.

3. The system of claim 2, wherein the retention member comprises a flange or a series of flanges that is integral with the housing.

4. The system of claim 2, wherein the retention member comprises a flange or a series of flanges that is discrete from the housing.

5. The system of claim 2, wherein the retention member comprises a series of flanges extending around the outer side wall of the at least one of the first and second elongated magnetic implants, the flanges being provided in a spaced-apart relationship relative to one another.

6. The system of claim 2, wherein the retention member and the housing are made of a same material.

7. The system of claim 2, wherein the retention member and the housing are made of a different material.

8. The system of claim 1, wherein the retention member comprises a flange or a series of flanges.

9. The system of claim 8, wherein the flange extends continuously around substantially an entire periphery of the outer side wall of the at least one of the first and second elongated magnetic implants.

10. The system of claim 1, wherein the retention member comprises a continuous rim extending circumferentially around the outer side wall of the at least one of the first and second elongated magnetic implants.

11. The system of claim 10, wherein the retention member has a T-shaped cross-section.

12. The system of claim 1, wherein the retention member comprises at least one of a bioerodible material, a biodegradable material, and a bioresorbable material.

13. The system of claim 1, wherein the retention member comprises at least two materials, the at least two materials having a different dissolution rate or a different degradation rate once implanted in a given environment.

14. The system of claim 1, wherein the retention member comprises at least one notch or spot having a dissolution rate or a degradation rate that is different from a remainder thereof once implanted in a given environment.

15. The system of claim 1, wherein each one of the first and second elongated magnetic implants comprises a corresponding retention member extending outwardly therefrom, the corresponding retention member of the first and second elongated magnetic implants being made of a same material.

16. The system of claim 1, wherein each one of the first and second elongated magnetic implants comprises a corresponding retention member extending outwardly therefrom, the corresponding retention member of the first magnetic implant being made from a different material than the corresponding retention member of the second magnetic implant.

17. The system of claim 16, wherein the first elongated magnetic implant is configured for implantation in a strongly acidic environment and the second elongated magnetic implant is configured for implantation in a weakly acidic environment, and once implanted in the strongly acidic environment and in the weak acidic environment respectively, the first and second elongated retention member have a similar dissolution rate or degradation rate.

18. The system of claim 1, wherein the outwardly-extending inner surface of the retention member is substantially flat.

19. The system of claim 1, wherein the outwardly-extending inner surface of the retention member comprises a curvature.

20. The system of claim 1, wherein each one of the first and second elongated magnetic implants comprises a corresponding retention member the corresponding retention members being provided such that a gap is defined between the outwardly-extending inner surfaces of the corresponding retention members of the first and second elongated magnetic implants once implanted in the digestive tract.

21. The system of claim 1, wherein the retention member comprises a portion that is foldable against the at least one of the first and second elongated magnetic implants for delivery within the digestive tract, the foldable portion being configured to unfurl once the at least one of the first and second elongated magnetic implants is implanted within the digestive tract.

22. The system of claim 1, wherein the retention member is configured to adopt a retracted configuration for delivery within the digestive tract, and an expanded configuration once the at least one of the first and second elongated magnetic implants is implanted within the digestive tract.

23. A system for forming an anastomosis between two adjacent walls of a digestive tract, the system comprising:
first and second elongated magnetic implants each comprising an outer side wall and a tissue-contacting portion extending inwardly from a compression perimeter defined by the outer side wall, the first and second elongated magnetic implants being configured to magnetically couple to each other through the two adjacent walls of the digestive tract to compress a portion of the two adjacent walls therebetween and form a necrotic area that becomes surrounded by a scarred edge following a healing time period, the tissue-contacting portion of the first elongated magnetic implant comprising:
a standoff feature being configured to maintain a space between respective tissue-contacting portions of the first and second elongated magnetic implants when the standoff feature contacts the tissue-contacting portion of the second elongated magnetic implant;
a retention member extending outwardly from the outer wall of at least one of the first and second elongated magnetic implants to define a retention member perimeter that is larger than the compression perimeter, the retention member being configured to retain the first and second elongated magnetic implants in position and prevent passage thereof through the necrotic area during the healing time period.

24. The system of claim 23, wherein the standoff feature includes a plurality of standoff features provided in a spaced-apart relationship.

25. The system of claim 23, wherein the tissue-contacting portion of the second elongated magnetic implant is substantially flat.

26. The system of claim 23, wherein the tissue-contacting portion of the second elongated magnetic implant comprises a recess having a shape that is complimentary to the standoff feature, the standoff feature having a higher height than a depth of the recess.

27. The system of claim 23, wherein the standoff feature comprises angled sides walls.

28. The system of claim 23, wherein the standoff feature comprises sides walls provided at a substantially right angle.

29. The system of claim 23, wherein the standoff feature is configured to provide a focal pressure gradient therearound.

\* \* \* \* \*